(12) United States Patent
Trabanco-Suárez et al.

(10) Patent No.: US 9,845,326 B2
(45) Date of Patent: Dec. 19, 2017

(54) SUBSTITUTED 3,4-DIHYDROPYRROLO[1,2-A]PYRAZINES AS BETA-SECRETASE (BACE) INHIBITORS

(75) Inventors: Andrés Avelino Trabanco-Suárez, Toledo (ES); Francisca Delgado-Jiménez, Toledo (ES)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 14/003,901

(22) PCT Filed: Mar. 7, 2012

(86) PCT No.: PCT/EP2012/053863
§ 371 (c)(1),
(2), (4) Date: Sep. 9, 2013

(87) PCT Pub. No.: WO2012/120023
PCT Pub. Date: Sep. 13, 2012

(65) Prior Publication Data
US 2013/0345228 A1    Dec. 26, 2013

(30) Foreign Application Priority Data
Mar. 9, 2011 (EP) .................................... 11157418

(51) Int. Cl.
A61K 31/4985    (2006.01)
C07D 487/04    (2006.01)

(52) U.S. Cl.
CPC .................. C07D 487/04 (2013.01)

(58) Field of Classification Search
CPC .......................... A61K 31/4985; C07D 487/04
USPC .......................................... 514/249; 544/349
See application file for complete search history.

(56) References Cited

U.S. PATENT DOCUMENTS

| | | | |
|---|---|---|---|
| 4,188,389 A | 2/1980 | Jirkovsky | |
| 5,292,732 A | 3/1994 | Rover | |
| 8,207,164 B2 | 6/2012 | Holzer | |
| 2005/0282825 A1 | 12/2005 | Malamas | |
| 2007/0005404 A1 | 1/2007 | Raz | |
| 2007/0225372 A1 | 9/2007 | Bueno Melendo | |
| 2008/0051420 A1 | 2/2008 | Berg | |
| 2009/0082560 A1 | 3/2009 | Kobayashi | |
| 2011/0009395 A1 | 1/2011 | Audia et al. | |
| 2012/0238557 A1 | 9/2012 | Masui et al. | |
| 2012/0277244 A1 | 11/2012 | Tintelnot-Blomley | |
| 2014/0256715 A1 | 9/2014 | Hurth et al. | |
| 2016/0152581 A1 | 6/2016 | Trabanco-Suarez et al. | |

FOREIGN PATENT DOCUMENTS

| CA | 2825620 | * | 9/2012 |
|---|---|---|---|
| EP | 2147914 | | 1/2010 |
| EP | 2 518 059 | | 10/2012 |
| JP | 2013-513563 | | 4/2013 |
| JP | 2012-147763 | | 7/2014 |
| JP | 2014-505688 | | 3/2015 |
| WO | WO 1998/057641 | | 12/1998 |
| WO | WO2003089434 | | 10/2003 |
| WO | WO2004026877 | | 4/2004 |
| WO | WO2004058176 | | 7/2004 |
| WO | WO2005037832 | | 4/2005 |
| WO | WO2006034093 A2 | | 3/2006 |
| WO | WO2006076842 | | 7/2006 |
| WO | WO 2006/138265 | | 12/2006 |

(Continued)

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Hackam, et al. JAMA, 296(14), 2006, 1731-1732.*
Esterhazy et al__Cell Metabolism, "Bace2 is a β Cell-Enriched Protease that Regulates Pancreatic β Cell Function and Mass",__ 2011__14__365-377.
Fleck et al. 2012, Curr. Alzheimer Res., "Bace1Dependent Neuregulin Processing: review" 9, 178-183.
Hackam, et al. JAMA, "Translation of Research Evidence From animals to Humans", 296(14), 2006, 1731-1732.
Haniu et al., 2000, J. Biol. Chem., "Protein Structure and folding: Characterization of Alzheimer's β-secretase protein BACE: a Pepsin Family member with Unusual Properties", 275, 21099-21106.
Hemming et al. 2009, PLoS ONE, "Identification of β-Secretase (BACE1) Substrates using Quantitative Proteomics", 4, e8477.
Hong et al, 2000, Science, "Structure of the Protease domain of memapsin 2(β-Secretase) Complexed with Inhibitor" 290, 150-153.
Jonsson et al. 2012, Nature, "A mutation in APP protects against Alzheimer's disease and age-related cognitive decline", 488, 96-99.
Kim et al. 2011, J. Biol. Chem. "Molecular Bases of Disease: Reduced Sodium Channel Nav1.1 Levels in BACE1-null Mice", 286, 8106-8116.
Koike H et al.,J Biochem., "Thimet Oligopeptidase Cleaves the Full-Length Alzheimer Amyloid Precursor Protein at a β-Secretase Cleavage Site in COS Cells" 1999, 126, 235-42.

(Continued)

Primary Examiner — Douglas M Willis

(74) Attorney, Agent, or Firm — Yuriy P. Stercho

(57) ABSTRACT

The present invention relates to novel 3,4-dihydro-pyrrolo [1,2-a]pyrazin-1-ylamine derivatives of formula (I)

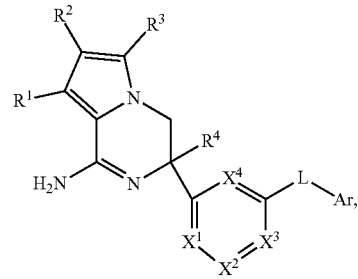

wherein $R^1$, $R^2$, $R^3$, $R^4$, $X^1$, $X^2$, $X^3$, $X^4$, L, and Ar are defined in the specification, as inhibitors of beta-secretase, also known as beta-site amyloid cleaving enzyme, BACE, BACE1, Asp2, or memapsin2. The invention is also directed to pharmaceutical compositions comprising such compounds, to processes for preparing such compounds and compositions, and to the use of such compounds and compositions for the prevention and treatment of disorders in which beta-secretase is involved, such as Alzheimer's disease (AD), mild cognitive impairment, senility, dementia, dementia with Lewy bodies, Down's syndrome, dementia associated with stroke, dementia associated with Parkinson's disease or dementia associated with beta-amyloid.

8 Claims, No Drawings

(56) References Cited

FOREIGN PATENT DOCUMENTS

| | | |
|---|---|---|
| WO | WO2007058583 A2 | 5/2007 |
| WO | WO2007114771 A1 | 10/2007 |
| WO | WO2007138265 A2 | 12/2007 |
| WO | WO2009022961 A1 | 2/2009 |
| WO | WO2009058300 A1 | 5/2009 |
| WO | WO2009097278 A1 | 8/2009 |
| WO | WO2009102468 A1 | 8/2009 |
| WO | WO2009134617 A1 | 11/2009 |
| WO | WO 2007/005404 | 1/2010 |
| WO | WO2011002409 A1 | 1/2011 |
| WO | WO2011009943 A1 | 1/2011 |
| WO | WO2011020806 A1 | 2/2011 |
| WO | WO 2011/069934 | 6/2011 |
| WO | WO2011071135 A1 | 6/2011 |
| WO | WO2011080176 A1 | 7/2011 |
| WO | WO 2011/154374 | 12/2011 |
| WO | WO2011154431 A1 | 12/2011 |
| WO | WO 2012/000933 | 1/2012 |
| WO | WO 2012/038438 | 3/2012 |
| WO | WO2012057247 A1 | 5/2012 |
| WO | WO2012085038 A1 | 6/2012 |
| WO | WO 2012/095463 | 7/2012 |
| WO | WO 2012/098064 | 7/2012 |
| WO | WO2012117027 A1 | 9/2012 |
| WO | WO2012120023 A1 | 9/2012 |
| WO | WO 2012/147763 | 11/2012 |
| WO | WO 2013/083556 | 6/2013 |
| WO | WO 2013/083557 | 6/2013 |
| WO | WO 2014/099794 | 6/2014 |
| WO | WO 2014/198851 | 12/2014 |
| WO | WO 2014/198853 | 12/2014 |
| WO | WO 2014/198854 | 12/2014 |
| WO | WO 2016/096979 | 6/2016 |

OTHER PUBLICATIONS

Kondoh et al. Breast Cancer Res.Treat., "A novel aspartic protease gene, ALP56, is up-regulated in human breast cancer independently from the cathepsin D gene", 2003, vol. 78, pp. 37-44.
Kuhn et al. 2012, EMBO J. "Secretome protein enrichment identifies physiological BACE1protease substrates in neurons" 31, 3157-3168.
Kuhn et al. J. Biol. Chem."Protein Synthesis, Post-translation Modification, and Degradation: Regulated Intramembrane Proteolysis of the Interleukin-1 receptor II by α-,β-, and γ-Secretase", 2007, vol. 282, No. 16, pp. 11982-11995.
Luo et al., 2001, Nat. Neurosci, "Mice deficient in BACE!, the Alzheimer's β-secretase, have normal phenotype and abolished β-amyloid generation", 4, 231-232.
Naus et al. 2004, J. Biol. Chem.,"Enzyme Catalysis and Regulation: Extodomain Shedding of the Neural Recognition Molecule CHL1 by the Metalloprotease-disintegrin ADAM8 Promotes Neurite Outgrowth and Suppresses Neuronal Cell Death", 279, 16083-16090.
Ostermann et al, 2006, Journal of molecular biology, "Crystal Structure of Human BACE2 in Complex with a Hydroxyethylamine transition-state Inhibitor", 355, (2), 249-61.
Patani et al, Chem.Rev., "Bioisosterism: A Rational Approach in Drug Design", 1996, 96, 3147-3176.
Roberds et al., 2001, Hum. Mol. Genet, "BACE knockout mice are healthy despite lacking the primary β-secretase activity in the brain: implications for Alzheimer's disease therapeutics",10, 1317-1324.
Rochin et al. PNAS, "BACE2 processes PMEL to form the melanosome amyloid matrix in pigment cells", Jun. 25, 2013, vol. 110, No. 26, pp. 10658-10663.
Silvestri_Medicinal Research Reviews, "Boom in the development of Non-Peptidic β-secretase (BACE1) Inhibitors for the Treatment of Alzheimer's Disease", 295-238_2009.

Stutzer et al. 2013, J. Biol. Chem., "Systematic Proteomic Analysis Identifies β-Site Amyloid Precursor Protein Cleaving Enzyme 2 and 1 (BACE2 and BACE1) Substrates in Pancreatic β-Cells" 288, 10536-10547.
Cheret et al. 2013 EMBO Journal, "Bace1 and Nueregulin-1 cooperate to control formation and maintenance of muscle spindles", (2013), 32(14), 2015-2028.
Jordan, V. C. Nature Reviews: Drug Discovery,"Tamoxifen: A Most Unlikely Pioneering Medicine", 2, 2003, 205.
Vassar et al., J. Neurochem., "Function, therapeutic potential and cell biology of BACE proteases: current status and future prospects", (2014) 10.1111/jnc.12715.
Vippagunta, et al. Advanced Drug Delivery Reviews, "Crystalline Solids", 48, 2001, 18.
Wang et al. Trends in Pharmacological Sciences, Apr, "β-Secretase: its biology as a therapeutic target in diseases", 2013, vol. 34, No. 4, pp. 215-225.
Willem et al. 2009, Semin. Cell Dev. Biol., Function, regulation and therapeutic properties of β-secretase (BACE1) 20, 175-182.
Yan and Vassar Lancet Neurol. "Targeting the β secretase BACE1 for Alzheimer's disease therapy", 2014, vol. 13, pp. 319-329.
Yan et al. J Alzheimers Dis. "Can BACE! Inhibition Mitigate Early Axonal Pathology in Neurological Diseases?", 2014, 30 vol. 38, No. 4, pp. 705-718.
Zhou et al. 2012, J. Biol. Chem. "The Neural Cell Adhesion Molecules L1 and CHL1 are Cleaved by BACE1 Protease in Vivo", 287, 25927-25940.
Sheridean, R.P., et al., "The Most Common Chemical Replacements in Drug-Like Compounds", J. Chem. Inf. Comput. Sci., 2002, vol. 42, pp. 103-108.
J. G. Cannon, Chapter Nineteen in Burger's Medicinal Chemistry and Drug Discovery, Fifth edition, vol. I: Principles and Practice, Wiley-Interscience 1995, pp. 783-802, 784.
Purser, et al., "Flourine in Medicinal Chemistry", Chemical Society Reviews, 2008, vol. 37, pp. 320-330.
Park, et al., "Metabolism of Fluorine-Containing Drugs", Annual Ref. Pharmacol. Toxicol. 2001, vol. 41, pp. 443-470.
Park, et al., Effects of Flourine Substitution on Drug Metabolism: Pharmacological and Toxicological Implicatins*, Drug metabolism reviews, vol. 26(3), 1994, pp. 605-643.
Wang, et al., Fluroine in Pharmaceutical Industry: Flourine-Containing Drugs Introduced to the Market in the Last Decade (2001-2011).
Hilpert, et al., "β-Secretase (BACE1) Inhibitors with High in vivo efficacy Suitable for Clinical Evaluation in Alzheimer's Disease", Journal of Medicinal Chemistry, vol. 56, No. 10, pp. 3980-3995, 2013.
Woltering, et al., "BACE Inhibitors: A head group scan on a series of amides:", Biorganic & Medicinal Chemistry Letters, vol. 23, pp. 4239-4243, 2013.
Ginman, et al., "Core refinement toward Permeable β-Secretase (BACE-1) Inhibitors with Low HERG Activity", Journal of Medicinal Chemistry, vol. 56, pp. 4181-4205, 2013.
Zhang, et al, "Application of Amybidbeta Protein in the Diagnosis of Alzheimer's Disease", vol. 29, No. 1, 2008.
Martic-Kehl et al., Eur J. Nucl Med Mol Imaging (2012) 39:1492-1496.
Mateu et al., Chem. Eur. J. 2015, 21, 11719-11726.
Oehlrich et al. The evolution of amidine-based brain penetrant BACE1 inhibitors_Bioorganic & Medicinal Chemistry Letters, 2014, vol. 24, pp. 2033-2045.
NIH National Institute on Aging, Aug. 2016, https://www.nia.nih.gov/alzheimers/publication/alheimers-disease-fact-sheet, NIH Publication No. 16-AG-6423.

* cited by examiner

SUBSTITUTED 3,4-DIHYDROPYRROLO[1,2-A]PYRAZINES AS BETA-SECRETASE (BACE) INHIBITORS

CROSS REFERENCE TO RELATED APPLICATIONS

This application is the national stage of PCT Application No. PCT/EP2012/053863 filed Mar. 7, 2012, which claims priority from European Patent Application No. 11157418.2, filed Mar. 9, 2011, the entire disclosures of which are hereby incorporated in their entirety.

FIELD OF THE INVENTION

The present invention relates to novel 3,4-dihydro-pyrrolo[1,2-a]pyrazin-1-ylamine derivatives as inhibitors of beta-secretase, also known as beta-site amyloid cleaving enzyme, BACE, BACE1, Asp2, or memapsin2. The invention is also directed to pharmaceutical compositions comprising such compounds, to processes for preparing such compounds and compositions, and to the use of such compounds and compositions for the prevention and treatment of disorders in which beta-secretase is involved, such as Alzheimer's disease (AD), mild cognitive impairment, senility, dementia, dementia with Lewy bodies, Down's syndrome, dementia associated with stroke, dementia associated with Parkinson's disease or dementia associated with beta-amyloid.

BACKGROUND OF THE INVENTION

Alzheimer's Disease (AD) is a neurodegenerative disease associated with aging. AD patients suffer from cognition deficits and memory loss as well as behavioral problems such as anxiety. Over 90% of those afflicted with AD have a sporadic form of the disorder while less than 10% of the cases are familial or hereditary. In the United States, about 1 in 10 people at age 65 have AD while at age 85, 1 out of every two individuals are affected with AD. The average life expectancy from the initial diagnosis is 7-10 years, and AD patients require extensive care either in an assisted living facility which is very costly or by family members. With the increasing number of elderly in the population, AD is a growing medical concern. Currently available therapies for AD merely treat the symptoms of the disease and include acetylcholinesterase inhibitors to improve cognitive properties as well as anxiolytics and antipsychotics to control the behavioral problems associated with this ailment.

The hallmark pathological features in the brain of AD patients are neurofibrillary tangles which are generated by hyperphosphorylation of tau protein and amyloid plaques which form by aggregation of beta-amyloid 1-42 (Abeta 1-42) peptide. Abeta 1-42 forms oligomers and then fibrils, and ultimately amyloid plaques. The oligomers and fibrils are believed to be especially neurotoxic and may cause most of the neurological damage associated with AD. Agents that prevent the formation of Abeta 1-42 have the potential to be disease-modifying agents for the treatment of AD. Abeta 1-42 is generated from the amyloid precursor protein (APP), comprised of 770 amino acids. The N-terminus of Abeta 1-42 is cleaved by beta-secretase (BACE), and then gamma-secretase cleaves the C-terminal end. In addition to Abeta 1-42, gamma-secretase also liberates Abeta 1-40 which is the predominant cleavage product as well as Abeta 1-38 and Abeta 1-43. These Abeta forms can also aggregate to form oligomers and fibrils. Thus, inhibitors of BACE would be expected to prevent the formation of Abeta 1-42 as well as Abeta 1-40, Abeta 1-38 and Abeta 1-43 and would be potential therapeutic agents in the treatment of AD.

SUMMARY OF THE INVENTION

The present invention is directed to a compound of Formula (I)

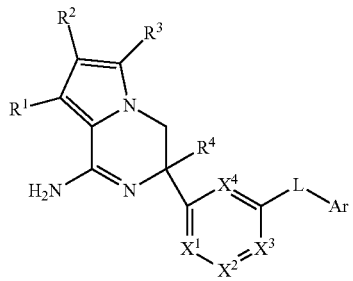

or a tautomer or a stereoisomeric form thereof, wherein
$R^1$, $R^2$, $R^3$ are independently selected from the group consisting of hydrogen, halo, cyano, $C_{1-3}$alkyl, mono- and polyhalo-$C_{1-3}$alkyl, and $C_{3-6}$cycloalkyl;
$R^4$ is selected from the group consisting of hydrogen, $C_{1-3}$alkyl, methoxymethyl, $C_{3-6}$cycloalkyl, mono- and polyhalo-$C_{1-3}$alkyl, homoaryl, and heteroaryl;
$X^1$, $X^2$, $X^3$, $X^4$ are independently $C(R^5)$ or N, provided that no more than two thereof represent N; $R^5$ is selected from the group consisting of hydrogen, halo, cyano, $C_{1-3}$alkyl, mono- and polyhalo-$C_{1-3}$alkyl, and $C_{3-6}$cycloalkyl;
L is a bond or —NHCO—;
Ar is homoaryl or heteroaryl;
wherein homoaryl is phenyl or phenyl substituted with one, two or three substituents selected from the group consisting of halo, cyano, $C_{1-3}$alkyl, $C_{1-3}$alkyloxy, mono- and polyhalo-$C_{1-3}$alkyl, and mono- and polyhalo-$C_{1-3}$alkyloxy;
heteroaryl is selected from the group consisting of pyridyl, pyrimidyl, pyrazinyl, pyridazyl, furanyl, thienyl, pyrrolyl, pyrazolyl, imidazolyl, triazolyl, thiazolyl, thiadiazolyl, oxazolyl, and oxadiazolyl, each optionally substituted with one, two or three substituents selected from the group consisting of halo, cyano, $C_{1-3}$alkyl, $C_{1-3}$alkyloxy, mono- and polyhalo-$C_{1-3}$alkyl, and mono- and polyhalo-$C_{1-3}$alkyloxy; or
an addition salt or a solvate thereof.

Illustrative of the invention is a pharmaceutical composition comprising a pharmaceutically acceptable carrier and any of the compounds described above. An illustration of the invention is a pharmaceutical composition made by mixing any of the compounds described above and a pharmaceutically acceptable carrier. Illustrating the invention is a process for making a pharmaceutical composition comprising mixing any of the compounds described above and a pharmaceutically acceptable carrier.

Exemplifying the invention are methods of treating a disorder mediated by the beta-secretase enzyme, comprising administering to a subject in need thereof a therapeutically effective amount of any of the compounds or pharmaceutical compositions described above.

Further exemplifying the invention are methods of inhibiting the beta-secretase enzyme, comprising administering to a subject in need thereof a therapeutically effective amount of any of the compounds or pharmaceutical compositions described above.

An example of the invention is a method of treating a disorder selected from the group consisting of Alzheimer's disease, mild cognitive impairment, senility, dementia, dementia with Lewy bodies, Down's syndrome, dementia associated with stroke, dementia associated with Parkinson's disease and dementia associated with beta-amyloid, preferably Alzheimer's disease, comprising administering to a subject in need thereof, a therapeutically effective amount of any of the compounds or pharmaceutical compositions described above.

Another example of the invention is any of the compounds described above for use in treating: (a) Alzheimer's Disease, (b) mild cognitive impairment, (c) senility, (d) dementia, (e) dementia with Lewy bodies, (f) Down's syndrome, (g) dementia associated with stroke, (h) dementia associated with Parkinson's disease and (i) dementia associated with beta-amyloid, in a subject in need thereof.

DETAILED DESCRIPTION OF THE INVENTION DETAILED DESCRIPTION OF THE INVENTION

The present invention is directed to compounds of Formula (I) as defined hereinbefore and pharmaceutically acceptable salts and solvates thereof. The compounds of Formula (I) are inhibitors of the beta-secretase enzyme (also known as beta-site cleaving enzyme, BACE, BACE1, Asp2 or memapsin 2), and are useful in the treatment of Alzheimer's disease, mild cognitive impairment, senility, dementia, dementia associated with stroke, dementia with Lewy bodies, Down's syndrome, dementia associated with Parkinson's disease and dementia associated with beta-amyloid, preferably Alzheimer's disease, mild cognitive impairment or dementia, more preferably Alzheimer's disease.

In an embodiment of the invention, $R^1$, $R^2$, $R^3$ are independently selected from the group consisting of hydrogen, halo, cyano, $C_{1-3}$alkyl, mono- and polyhalo-$C_{1-3}$alkyl, and $C_{3-6}$cycloalkyl;

$R^4$ is selected from the group consisting of hydrogen, $C_{1-3}$alkyl, $C_{3-6}$cycloalkyl, mono- and polyhalo-$C_{1-3}$alkyl, homoaryl, and heteroaryl;

$X^1$, $X^2$, $X^3$, $X^4$ are independently $C(R^5)$ or N, provided that no more than two thereof represent N; $R^5$ is selected from the group consisting of hydrogen, halo, cyano, $C_{1-3}$alkyl, mono- and polyhalo-$C_{1-3}$alkyl, and $C_{3-6}$cycloalkyl;

L is a bond or —NHCO—;

Ar is homoaryl or heteroaryl;

wherein homoaryl is phenyl or phenyl substituted with one, two or three substituents selected from the group consisting of halo, cyano, $C_{1-3}$alkyl, $C_{1-3}$alkyloxy, mono- and polyhalo-$C_{1-3}$alkyl, and mono- and polyhalo-$C_{1-3}$alkyloxy;

heteroaryl is selected from the group consisting of pyridyl, pyrimidyl, pyrazinyl, pyridazyl, furanyl, thienyl, pyrrolyl, pyrazolyl, imidazolyl, triazolyl, thiazolyl, thiadiazolyl, oxazolyl, and oxadiazolyl, each optionally substituted with one, two or three substituents selected from the group consisting of halo, cyano, $C_{1-3}$alkyl, $C_{1-3}$alkyloxy, mono- and polyhalo-$C_{1-3}$alkyl, and mono- and polyhalo-$C_{1-3}$alkyloxy; or an addition salt or a solvate thereof.

In an embodiment of the present invention, $R^1$, $R^2$ and $R^3$ are independently selected from hydrogen and $C_{1-3}$alkyl;

$X^1$, $X^2$, $X^3$, $X^4$ are independently $C(R^5)$ wherein each $R^5$ is selected from hydrogen and halo;

L is a bond or —NHCO—;

Ar is homoaryl or heteroaryl;

wherein homoaryl is phenyl or phenyl substituted with one or two substituents selected from the group consisting of halo, cyano, $C_{1-3}$alkyl, $C_{1-3}$alkyloxy, and polyhalo-$C_{1-3}$alkyloxy;

heteroaryl is selected from the group consisting of pyridyl, pyrimidyl, and pyrazinyl, each optionally substituted with one or two substituents selected from the group consisting of halo, cyano, $C_{1-3}$alkyl, $C_{1-3}$alkyloxy, and polyhalo-$C_{1-3}$alkyloxy; or an addition salt or a solvate thereof.

In another embodiment of the present invention, $R^1$, $R^2$ and $R^3$ are hydrogen;

$X^1$ is CF;

$X^2$, $X^3$, $X^4$ are CH;

L is a bond or —NHCO—; Ar is homoaryl or heteroaryl;

wherein homoaryl is phenyl substituted with chloro;

heteroaryl is selected from the group consisting of pyridyl and pyrimidyl, each optionally substituted with one or two substituents selected from the group consisting of chloro, fluoro, cyano, methyl, and methoxy; or an addition salt or a solvate thereof.

In another embodiment, the carbon atom substituted with R4 has the R-configuration.

In an embodiment of the invention, $R^1$ and $R^3$ are hydrogen, $R^2$, is hydrogen, fluoro, or trifluoromethyl;

$R^4$ is methyl or difluoromethyl;

$X^1$ is CH or CF;

$X^2$, $X^3$, and $X^4$ are CH;

L is —NHCO—;

Ar is 5-chloropyridin-2-yl, 5-cyanopyridin-2-yl, 5-fluoropyridin-2-yl, 5-cyano-3-fluorooropyridin-2-yl, 5-methoxypyrazin-2-yl or 1-difluoromethylpyrazol-3-yl; or an addition salt or a solvate thereof.

DEFINITIONS

"Halo" shall denote fluoro, chloro and bromo; "$C_{1-3}$alkyl" shall denote a straight or branched saturated alkyl group having 1, 2 or 3 carbon atoms, e.g. methyl, ethyl, 1-propyl and 2-propyl; "$C_{1-3}$alkyloxy" shall denote an ether radical wherein $C_{1-3}$alkyl is as defined before; "mono- and polyhalo $C_{1-3}$alkyl" shall denote $C_{1-3}$alkyl as defined before, substituted with 1, 2 3 or where possible with more halo atoms as defined before; "mono- and polyhalo$C_{1-3}$alkyloxy" shall denote an ether radical wherein mono- and polyhalo$C_{1-3}$alkyl is as defined before; "$C_{3-6}$cycloalkyl" shall denote cyclopropyl, cyclobutyl, cyclopentyl and cyclohexyl; "$C_{3-6}$cycloalkanediyl" shall denote a bivalent radical such as cyclopropanediyl, cyclobutanediyl, cyclopentanediyl and cyclohexanediyl.

The term "subject" as used herein, refers to an animal, preferably a mammal, most preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

Hereinbefore and hereinafter, the term "compound of formula (I)" is meant to include the addition salts, the solvates and the stereoisomers thereof.

The terms "stereoisomers" or "stereochemically isomeric forms" hereinbefore or hereinafter are used interchangeably.

The compounds of Formula (I) coexist in a dynamic equilibrium with the compounds of Formula (I-1).

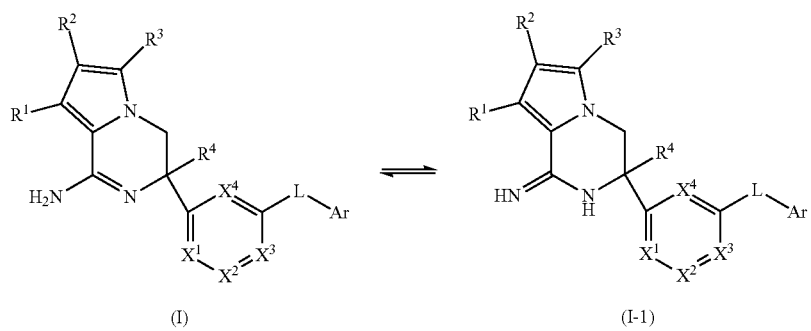

(I)            (I-1)

The invention includes all stereoisomers of the compound of Formula (I) either as a pure stereoisomer or as a mixture of two or more stereoisomers.

Enantiomers are stereoisomers that are non-superimposable mirror images of each other. A 1:1 mixture of a pair of enantiomers is a racemate or racemic mixture. Diastereomers (or diastereoisomers) are stereoisomers that are not enantiomers, i.e. they are not related as mirror images. If a compound contains a double bond, the substituents may be in the E or the Z configuration. If a compound contains a disubstituted cycloalkyl group, the substituents may be in the cis or trans configuration. Therefore, the invention includes enantiomers, diastereomers, racemates, E isomers, Z isomers, cis isomers, trans isomers and mixtures thereof.

The absolute configuration is specified according to the Cahn-Ingold-Prelog system. The configuration at an asymmetric atom is specified by either R or S. Resolved compounds whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other isomers. Thus, when a compound of formula (I) is for instance specified as (R), this means that the compound is substantially free of the (S) isomer; when a compound of formula (I) is for instance specified as E, this means that the compound is substantially free of the Z isomer; when a compound of formula (I) is for instance specified as cis, this means that the compound is substantially free of the trans isomer.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

For use in medicine, the salts of the compounds of this invention refer to non-toxic "pharmaceutically acceptable salts". Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

Representative acids which may be used in the preparation of pharmaceutically acceptable salts include, but are not limited to, the following: acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, capric acid, caproic acid, caprylic acid, cinnamic acid, citric acid, cyclamic acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, beta-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, trifluoromethyl-sulfonic acid, and undecylenic acid. Representative bases which may be used in the preparation of pharmaceutically acceptable salts include, but are not limited to, the following: ammonia, L-arginine, benethamine, benzathine, calcium hydroxide, choline, dimethylethanolamine, diethanolamine, diethylamine, 2-(diethylamino)-ethanol, ethanolamine, ethylene-diamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

The chemical names of the compounds of the present invention were generated according to the nomenclature rules agreed upon by the Chemical Abstracts Service.

A. Preparation of the Final Compounds

Experimental Procedure 1

The final compounds according to Formula (I), can be prepared by reacting an intermediate compound of Formula (II) with an appropriate source of ammonia such as, for example, ammonium chloride or aqueous ammonia, according to Reaction Scheme (1), a reaction that is performed in a suitable reaction-inert solvent, such as, for example, water or methanol, under thermal conditions such as, for example, heating the reaction mixture at 60 to 90° C., for example for 4 to 100 hours. In Reaction Scheme (1), all variables are defined as in Formula (I).

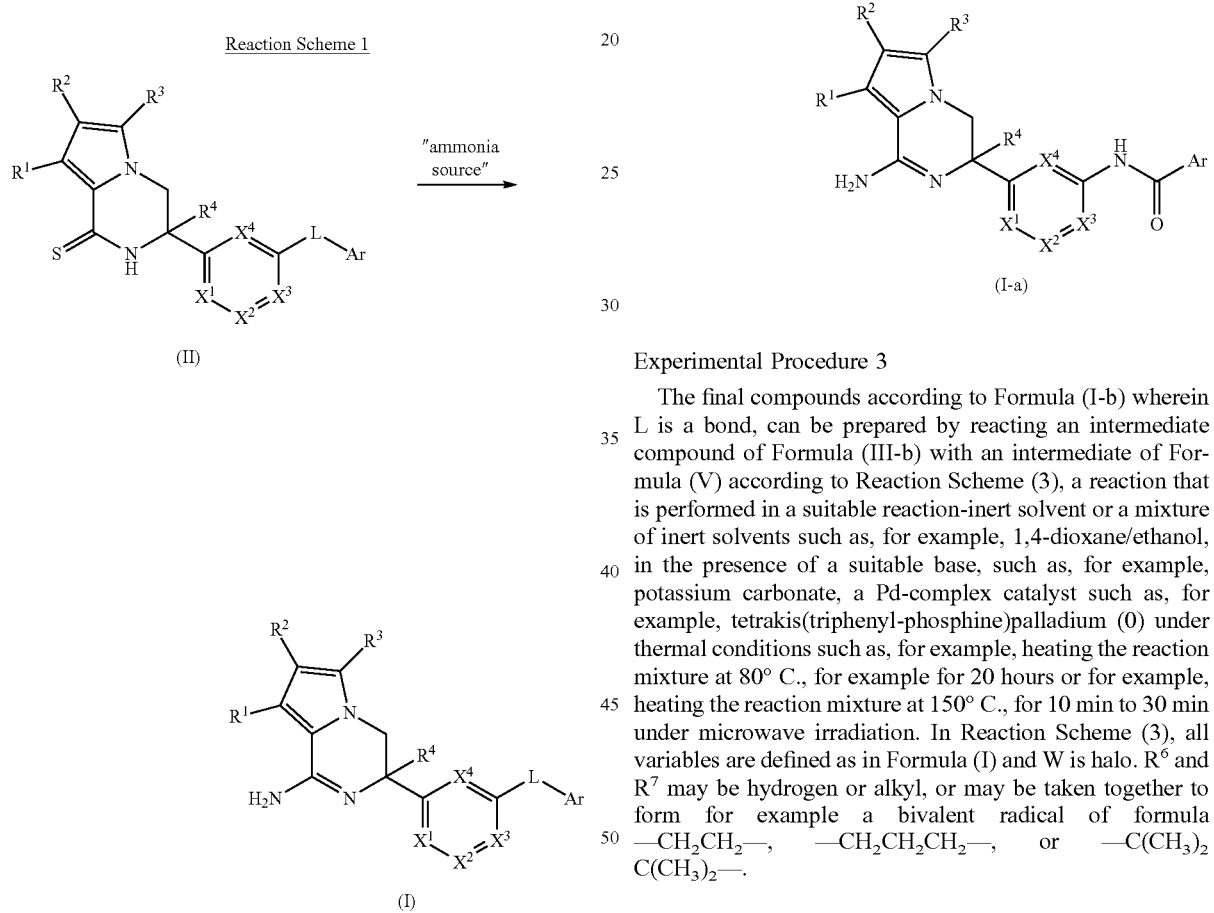

Experimental Procedure 2

Additionally, the final compounds according to Formula (I-a) wherein L is —NHCO—, can be prepared by reacting an intermediate compound of Formula (III-a) with an intermediate of Formula (IV) according to Reaction Scheme (2), a reaction that is performed in a suitable reaction-inert solvent, such as, for example, dichloromethane, in the presence of a condensation agent such as for example 4-(4,6-dimethoxy-1,3,5-triazin-2-yl)-4-methylmorpholinium chloride, under thermal conditions such as, for example, heating the reaction mixture at 25° C., for example for 2 hours. In Reaction Scheme (2), all variables are defined as in Formula (I).

Experimental Procedure 3

The final compounds according to Formula (I-b) wherein L is a bond, can be prepared by reacting an intermediate compound of Formula (III-b) with an intermediate of Formula (V) according to Reaction Scheme (3), a reaction that is performed in a suitable reaction-inert solvent or a mixture of inert solvents such as, for example, 1,4-dioxane/ethanol, in the presence of a suitable base, such as, for example, potassium carbonate, a Pd-complex catalyst such as, for example, tetrakis(triphenyl-phosphine)palladium (0) under thermal conditions such as, for example, heating the reaction mixture at 80° C., for example for 20 hours or for example, heating the reaction mixture at 150° C., for 10 min to 30 min under microwave irradiation. In Reaction Scheme (3), all variables are defined as in Formula (I) and W is halo. $R^6$ and $R^7$ may be hydrogen or alkyl, or may be taken together to form for example a bivalent radical of formula —$CH_2CH_2$—, —$CH_2CH_2CH_2$—, or —$C(CH_3)_2C(CH_3)_2$—.

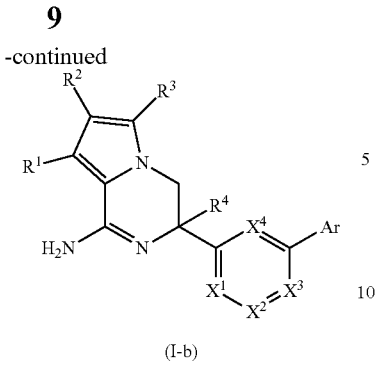

(I-b)

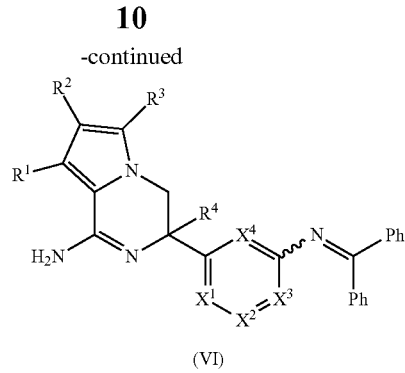

(VI)

|"acid"

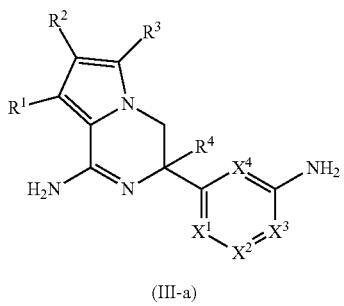

(III-a)

A number of intermediates and starting materials in the foregoing preparations are known compounds which may be prepared according to art-known methodologies of preparing said or similar compounds and some intermediates are new. A number of such preparation methods will be described hereinafter in more detail.

B. Preparation of the Intermediate Compounds

Experimental Procedure 4

The intermediates according to Formula (III-a) can be prepared from the corresponding intermediate compounds of Formula (III-b) following art-known Buchwald-Hartwig type coupling procedures followed by acidic hydrolysis according to Reaction Scheme (4). Said coupling may be conducted by treatment of intermediate compounds of Formula (III-b) with benzophenone imine in a suitable reaction-inert solvent, such as, for example, toluene, in the presence of a suitable base, such as, for example, sodium tert-butoxide, a Pd-complex catalyst such as tris(dibenzylideneacetone)dipalladium (0), under thermal conditions such as, for example, heating the reaction mixture at 100° C., for example for 2 hours. The resulting intermediate compound of Formula (VI) is then transformed into the intermediate compound of Formula (III-a) by treatment with a strong acid, such as for example, hydrochloric acid, in a suitable reaction-inert solvent, such as for example, isopropyl alcohol, under thermal conditions such as, for example, at 25° C., for example for 1 hour. Alternatively, an intermediate of Formula (III-a) can be obtained in one step starting from an intermediate of Formula (III-b), by mean of a copper-catalyzed coupling in the presence of sodium azide, a ligand for copper, such as N,N'-dimethyl-ethylenediamine, a suitable base, such as sodium carbonate, in a reaction inert solvent, such as DMSO, under thermal conditions such as heating the reaction mixture at 110° C. for 25 hours. In Reaction Scheme (4), all variables are defined as in Formula (I) and W is halo.

Experimental Procedure 5

The intermediates according to Formula (VII) can be prepared from the corresponding intermediates of Formula (VIII-c) following art-known nitro-to-amino reduction procedures according to Reaction Scheme (5). For example, said reduction may be carried out by stirring the reactants or passing them through a flow reactor under a hydrogen atmosphere and in the presence of an appropriate catalyst such as, for example, palladium-on-charcoal. Suitable solvents are, for example, water, alkanols, e.g. methanol, ethanol and the like, esters, e.g. ethyl acetate and the like. In order to enhance the rate of said reduction reaction it may be advantageous to elevate the temperature and/or the pressure of the reaction mixture. Undesired further hydrogenation of certain functional groups in the reactants and the reaction products may be prevented by the addition of a catalyst poison such as, for example, thiophene and the like, to the reaction mixture. In Reaction Scheme (5), all variables are defined as in Formula (I).

Reaction Scheme 4

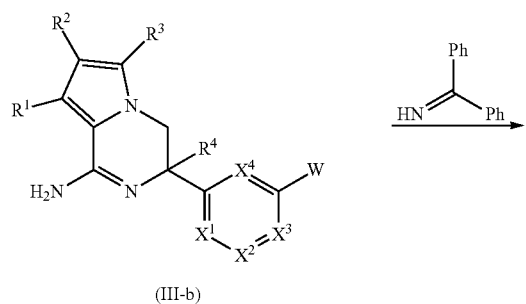

(III-b)

Reaction Scheme 5

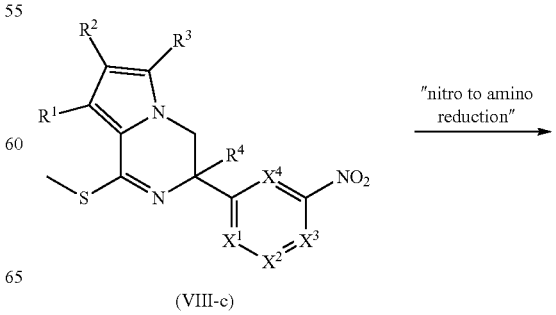

(VIII-c)

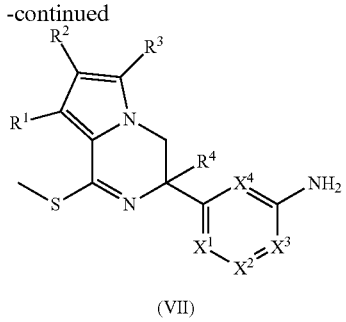

(VII)

Experimental Procedure 6

The intermediate compounds of Formula (III-a) can be prepared from intermediate compounds of Formula (VII) according to Reaction Scheme (6). Said conversion may conveniently be conducted by treatment of the said intermediate with an ammonia source such as, for example, ammonium chloride and ethanolic ammonia, under thermal conditions such as, for example, heating the reaction mixture at 80° C., for example for 72 hours. In Reaction Scheme (6) all variables are defined as in Formula (I).

Reaction Scheme 6

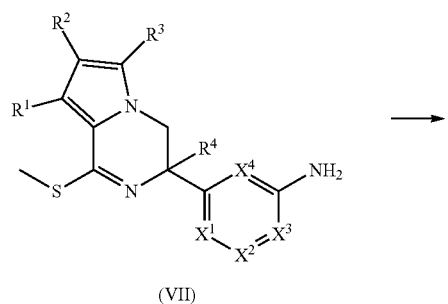

(VII)

→

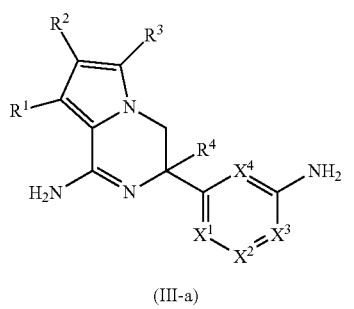

(III-a)

Experimental Procedure 7

An intermediate of Formula (IX) wherein L is —NHCO—, can be prepared by reacting an intermediate compound of Formula (VII) with an intermediate of Formula (IV) according to Reaction Scheme (7), a reaction that is performed in a suitable reaction-inert solvent, such as, for example, methanol, in the presence of a condensation agent such as for example, 4-(4,6-dimethoxy-1,3,5-triazin-2-yl)-4-methylmorpholinium chloride, under thermal conditions such as, for example, heating the reaction mixture at 25° C., for example for 3 hours. In Reaction Scheme (7), all variables are defined as in Formula (I).

Reaction Scheme 7

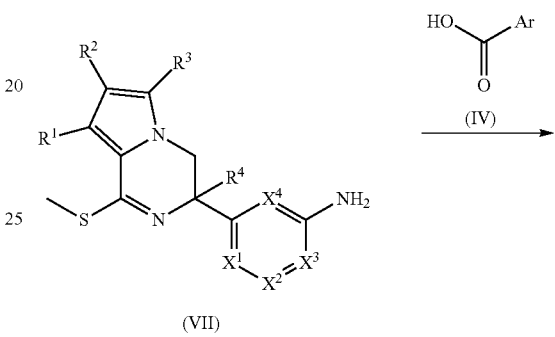

(VII)

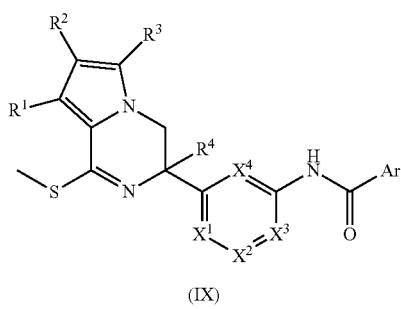

(IX)

Experimental Procedure 8

The intermediate compounds of Formula (III-b) and (III-c) can generally be prepared following the reaction steps shown in the Reaction Schemes (8) and (9) below.

Reaction Scheme 8
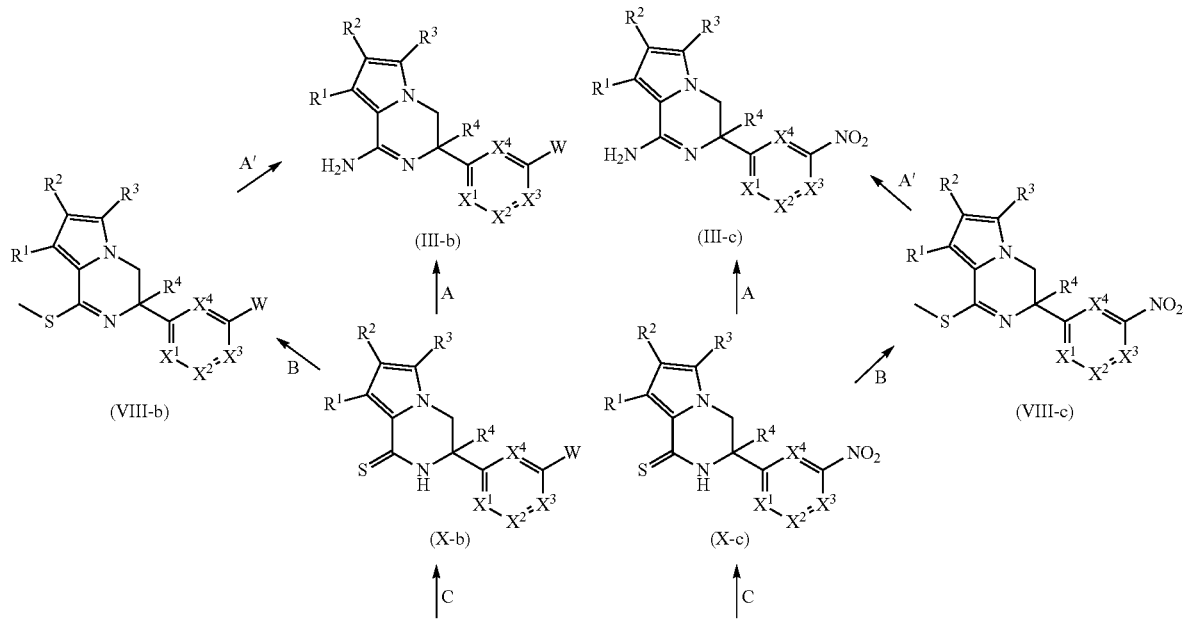
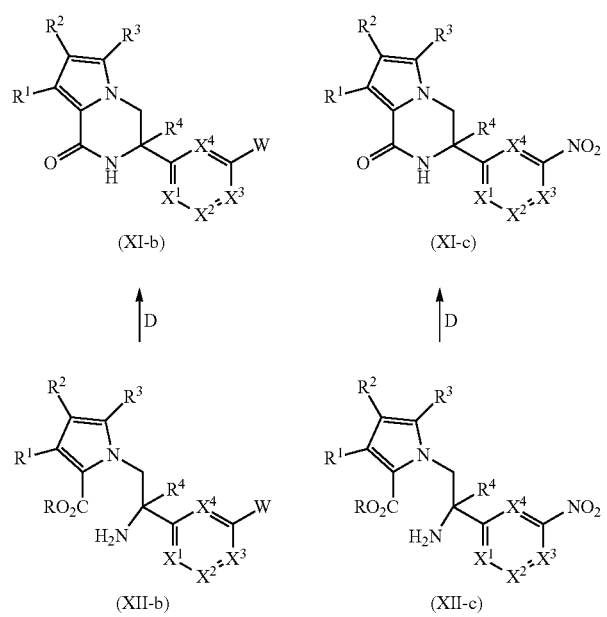

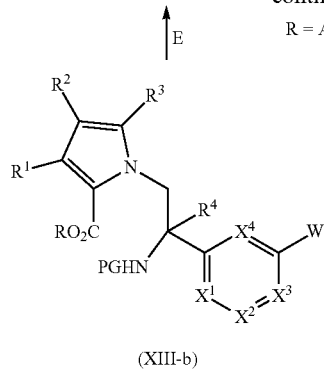

(XIII-b)

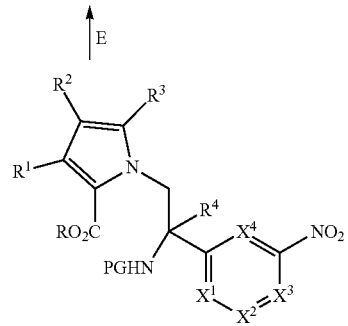

(XIII-c)

A: Thioamide-to-amidine converstion
A': Methyltio to amino conversion
B: Methylation of the sulfur
C: Amide-to-thioamide conversion (thionation)
D: Cyclization
E: Removing any N-protecting groups The amidine derivatives in the above Reaction Scheme (8) may be conveniently prepared from the corresponding thioamide derivatives following art-known thioamide-to-amidine conversion procedures (reaction step A). Said conversion may conveniently be conducted by treatment of the said thioamides with an ammonia source such as, for example, ammonium chloride or aqueous ammonia, in a suitable reaction-inert solvent such as, for example, water or methanol and the like, under thermal conditions such as, for example, heating the reaction mixture at 60 to 90° C., for example for 6 to 100 hours. Under similar conditions, also the methylated intermediates (VIII-b) and (VIII-c) can be converted into the desired amidines (reaction step A'). Intermediates (VIII-b) and (VIII-c) can be conveniently prepared starting from the corresponding thioamides, dissolved in a suitable solvent, such as acetone, in the presence of a base, such as potassium carbonate, and a methylating agent, such as methyl iodide, under thermal conditions such as room temperature for 3 hours (reaction step B).

The thioamide derivatives in the above Reaction Scheme (8) can be prepared from amide derivatives following art-known thionation procedures (reaction step C). Said conversion may conveniently be conducted by treatment of the said amides with a thionation agent such as, for example, phosphorous pentasulfide or 2,4-bis-(4-methoxy-phenyl)-1,3-dithia-2,4-diphosphetane 2,4-disulfide [Lawesson's reagent], in a reaction inert solvent such as, for example, tetrahydrofuran or 1,4-dioxane and the like, in the presence of a suitable base like pyridine under thermal conditions such as, for example, heating the reaction mixture at 50 to 100° C., for example for 24 hours.

The amide derivatives of Formula (XI-b) and (XI-c) in the above Reaction Scheme (8) can be prepared from the corresponding intermediate compounds of Formula (XII-b) and (XII-c) following art-known cyclization procedures (reaction step D). Said cyclization may conveniently be conducted by treatment of intermediate compounds of Formula (XII-b) and (XII-c) with a suitable base, such as potassium acetate or sodium methoxyde, in a suitable reaction solvent, such as for example ethanol and the like, at 55° C. to 100° C., for a period of time to ensure the completion of the reaction.

The intermediate compounds of Formula (XII-b) and (XII-c) in the above Reaction Scheme (8) can be prepared from the corresponding intermediate compounds of Formula (XIII-b) and (XII-c) by removal of the protecting group being carried out according to processes known in the art.

Experimental Procedure 9

Reaction Scheme 9

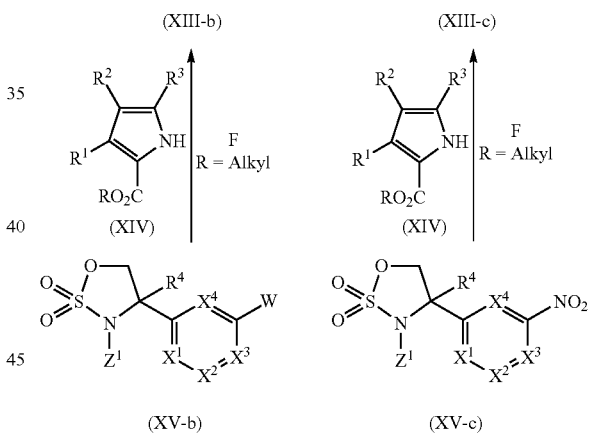

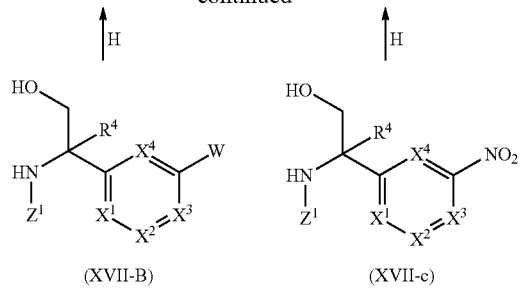

(XVII-B)    (XVII-c)

F: Alkylation
G: Oxathiazolidine oxidation
H: Oxathiazolidine formation

The intermediates according to Formula (XIII-b) and (XIII-c) in the above Reaction Scheme (9) can be prepared from the corresponding intermediate compounds of Formula (XV-b) and (XV-c), wherein $Z^1$ is a protecting group of amines such as, for example, the tert-butoxycarbonyl group, following art-known alkylation procedures (reaction step F). Said alkylation may conveniently be conducted by treatment of (XV-b) and (XV-c) respectively with the corresponding intermediate compounds of Formula (XIV) in the presence of a suitable base such as, for example, sodium carbonate or cesium carbonate, in a suitable inert solvent such as, for example,
N,N-dimethyl formamide or dimethoxysulfoxide, at low temperature such as, for example, 0° C. for 30 min and then at a moderately high temperature such as, for example, 100° C. for 24 hours to 100 hours or for example, heating the reaction mixture at 130° C., for example for 30 min to 45 min. under microwave irradiation.

The intermediates according to Formula (XV-b) and (XV-c) in the above Reaction Scheme (9) can be prepared by reacting the intermediate compounds of Formula (XVI-b) and (XVI-c) following art-known oxidation procedures (reaction step G). Said oxidation may conveniently be conducted by treatment of the corresponding intermediate compounds of Formula (XVI-b) and (XVI-c) with an oxidant agent such as, for example, sodium periodate in a suitable inert solvent such as, for example, acetonitrile/water, in the presence of ruthenium (III) chloride at a moderately high temperature such as, for example, 25° C., for example for 2 hours.

The intermediates according to Formula (XVI-b) and (XVI-c) in the above Reaction Scheme (9) can be prepared by reacting the intermediate compounds of Formula (XVII-b) and (XVII-c) following art-known sulfamidate formation procedures (reaction step H). Said transformation may conveniently be conducted by treatment of the corresponding intermediate compounds of Formula (XVII-b) and (XVII-c) with thionyl chloride, in the presence of a base such as, for example, pyridine, in a suitable reaction-inert solvent, such as, for example, acetonitrile, at low temperature such as, for example, −40° C., for example for 30 min and then at a moderately high temperature such as, for example, 25° C., for example for 24 to 72 hours.

The intermediates compounds of Formula (XVII-b) and (XVII-c), wherein $Z^1$ is a protecting group of amines such as, for example, the tert-butoxycarbonyl group, can generally be prepared following art-known Strecker type procedures described in literature.

Experimental Procedure 10

The intermediate compounds of Formula (XVIII) wherein Q is halo or nitro, can be prepared from intermediate compounds of Formula (XI-b) or (XI-c) according to Reaction Scheme (14), a reaction that is performed in a suitable reaction-inert solvent, such as for example, dichloromethane, in the presence of a methylating agent, such as for example, trimethyl-oxonium tetrafluoroborate, under thermal conditions, such as for example, at 25° C., for example for 4 days. Intermediate (XVIII) can then be further converted into amidines (III-b) and (III-c) by reaction with an ammonia source such as, for example, ammonium chloride and ethanolic ammonia, under thermal conditions such as, for example, heating the reaction mixture at 80° C., for example for 36 hours. In Reaction Scheme (10) all variables are defined as in Formula (I) and Q is halo or nitro.

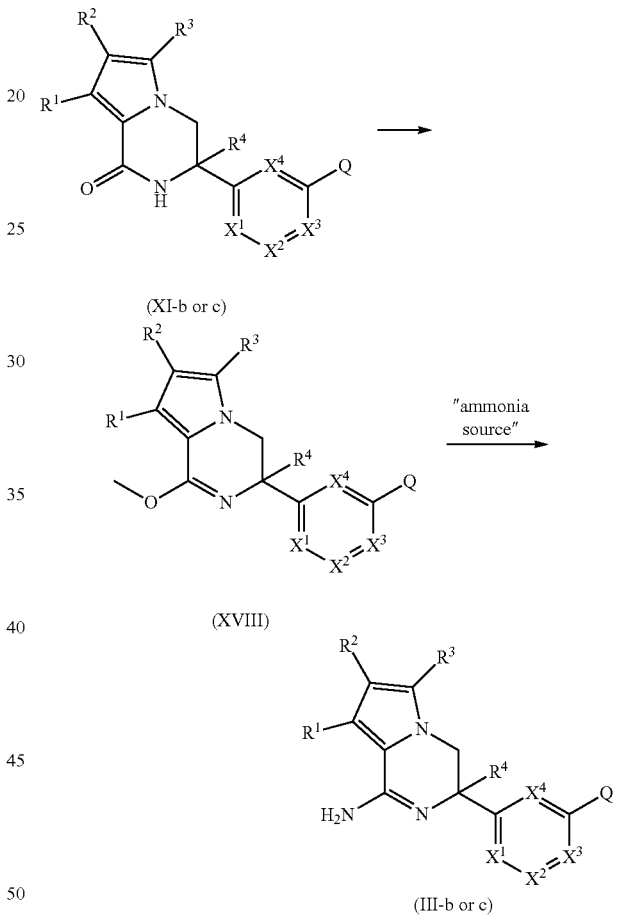

Reaction Scheme 10

Pharmacology

The compounds of the present invention and the pharmaceutically acceptable compositions thereof inhibit BACE and therefore may be useful in the treatment or prevention of Alzheimer's Disease (AD), mild cognitive impairment (MCI), senility, dementia, dementia with Lewy bodies, cerebral amyloid angiopathy, multi-infarct dementia, Down's syndrome, dementia associated with Parkinson's disease and dementia associated with beta-amyloid.

The invention relates to a compound according to the general Formula (I), a stereoisomeric form thereof or a pharmaceutically acceptable acid or base addition salt or a solvate thereof, for use as a medicament.

The invention also relates to a compound according to the general Formula (I), a stereoisomeric form thereof or a the pharmaceutically acceptable acid or base addition salt or a solvate thereof, for use in the treatment or prevention of diseases or conditions selected from the group consisting of AD, MCI, senility, dementia, dementia with Lewy bodies, cerebral amyloid angiopathy, multi-infarct dementia, Down's syndrome, dementia associated with Parkinson's disease and dementia associated with beta-amyloid.

The invention also relates to the use of a compound according to the general Formula (I), a stereoisomeric form thereof or a pharmaceutically acceptable acid or base addition salt or a solvate thereof, for the manufacture of a medicament for the treatment or prevention of any one of the disease conditions mentioned hereinbefore.

In view of the utility of the compound of Formula (I), there is provided a method of treating warm-blooded animals, including humans, suffering from or a method of preventing warm-blooded animals, including humans, to suffer from any one of the diseases mentioned hereinbefore.

Said methods comprise the administration, i.e. the systemic or topical administration, preferably oral administration, of an effective amount of a compound of Formula (I), a stereoisomeric form thereof, a pharmaceutically acceptable addition salt or solvate thereof, to a warm-blooded animal, including a human.

A method of treatment may also include administering the active ingredient on a regimen of between one and four intakes per day. In these methods of treatment the compounds according to the invention are preferably formulated prior to administration. As described herein below, suitable pharmaceutical formulations are prepared by known procedures using well known and readily available ingredients.

The compounds of the present invention, that can be suitable to treat or prevent Alzheimer's disease or the symptoms thereof, may be administered alone or in combination with one or more additional therapeutic agents. Combination therapy includes administration of a single pharmaceutical dosage formulation which contains a compound of Formula (I) and one or more additional therapeutic agents, as well as administration of the compound of Formula (I) and each additional therapeutic agents in its own separate pharmaceutical dosage formulation. For example, a compound of Formula (I) and a therapeutic agent may be administered to the patient together in a single oral dosage composition such as a tablet or capsule, or each agent may be administered in separate oral dosage formulations.

Pharmaceutical Compositions

The present invention also provides compositions for preventing or treating diseases in which inhibition of beta-secretase is beneficial, such as Alzheimer's disease (AD), mild cognitive impairment, senility, dementia, dementia with Lewy bodies, Down's syndrome, dementia associated with stroke, dementia associated with Parkinson's disease and dementia associated with beta-amyloid. Said compositions comprising a therapeutically effective amount of a compound according to formula (I) and a pharmaceutically acceptable carrier or diluent.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy. A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The exact dosage and frequency of administration depends on the particular compound of Formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

The present compounds can be used for systemic administration such as oral, percutaneous or parenteral administration; or topical administration such as via inhalation, a nose spray, eye drops or via a cream, gel, shampoo or the like. The compounds are preferably orally administered. The exact dosage and frequency of administration depends on the particular compound according to Formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

The amount of a compound of Formula (I) that can be combined with a carrier material to produce a single dosage form will vary depending upon the disease treated, the mammalian species, and the particular mode of administration. However, as a general guide, suitable unit doses for the compounds of the present invention can, for example, preferably contain between 0.1 mg to about 1000 mg of the active compound. A preferred unit dose is between 1 mg to about 500 mg. A more preferred unit dose is between 1 mg to about 300 mg. Even more preferred unit dose is between 1 mg to about 100 mg. Such unit doses can be administered more than once a day, for example, 2, 3, 4, 5 or 6 times a day, but preferably 1 or 2 times per day, so that the total dosage for a 70 kg adult is in the range of 0.001 to about 15 mg per kg weight of subject per administration. A preferred dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

The following examples are intended to illustrate but not to limit the scope of the present invention.

Experimental Part

Hereinafter, the term "AcOH" means acetic acid, "AcOEt" means ethyl acetate, "DCM" means dichloromethane, "DIPE" means diisopropylether, "DMF" means N,N-dimethylformamide, "DMSO" means dimethylsulfoxide, "Et$_2$O" means diethylether, "Et$_3$N" means triethylamine, "EtOH" means ethanol, "MeCN" means acetonitrile, "DCE" means 1,2-dichloroethane, "MeOH" means methanol, "m.p." means melting point, "rac" means racemic, "R$_f$" means retention time, "THF" means tetrahydrofuran, "K$_2$CO$_3$" means potassium carbonate, "NH$_3$" means ammonia, "NH$_4$Cl" means ammonium chloride, "HCl" means hydrochloric acid, "Na$_2$SO$_4$" means sodium sulphate, "NaHCO$_3$" means sodium bicarbonate, "KHSO$_4$" means potassium hydrogenosulphate, "MgSO$_4$" means magnesium sulphate, "H$_2$O" means water, "TFA" means trifluoroacetic acid, "sat." means saturated, "aq." means aqueous, "min" means min, "Pd$_2$(dba)$_3$" means tris(dibenzylideneacetone)dipalladium (0), "Pd(PPh$_3$)$_4$" means tetrakis(triphenylphosphine)palladium (0) "BINAP" means 2,2'-bis(diphenylphosphino)-1,1'-binaphthyl, "TBAF" means tetrabutylammonium fluoride, "NaH" means sodium hydride, "DDQ" means 2,3-dichloro-5,6-dicyano-1,4-benzoquinone, "DBU" means 1,8-diazabicyclo[5.4.0]undec-7-ene.

Microwave assisted reactions were performed in a single-mode reactor: Emrys™ Optimizer microwave reactor (Personal Chemistry A.B., currently Biotage).

Hydrogenation reactions were performed in a continuous flow hydrogenator H-CUBE® from ThalesNano Nanotechnology Inc.

Thin layer chromatography (TLC) was carried out on silica gel 60 F254 plates (Merck) using reagent grade solvents. Open column chromatography was performed on silica gel, particle size 60 Å, mesh=230-400 (Merck) under standard techniques. Flash column chromatography was performed using ready-to-connect cartridges from Merck, on irregular silica gel, particle size 15-40 µm (normal layer disposable flash columns) on a SPOT or LAFLASH system from Armen Instrument.

Optical rotations were measured on a Perkin-Elmer 341 polarimeter with a sodium lamp and reported as follows: [α]° (λ, c g/100 ml, solvent, T° C.).

A. Preparation of the Intermediates

Example A1

Preparation of Intermediate A1

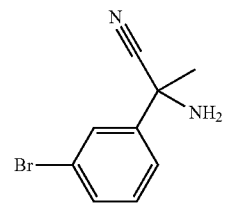

Trimethylsilylcyanide (20 g, 200 mmol) was added to a stirred solution of 3-bromo-acetophenone (20 g, 100 mmol) and NH$_4$Cl (11 g, 200 mmol) in NH$_3$/MeOH (400 mL). The mixture was stirred at room temperature for 4 days. Then the solvent was evaporated in vacuo and the residue was taken up in AcOEt (100 mL). The solid was filtered off and the filtrate was evaporated in vacuo to yield intermediate A1 (20 g, 86% yield), which was used in the next step without further purification.

Example A2

Preparation of Intermediate A2

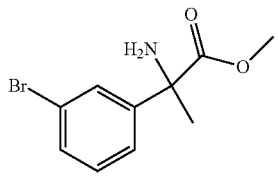

Intermediate A1 (20 g, 88.9 mmol) was dissolved in HCl/MeOH (500 mL). The mixture was refluxed for 4 days. After cooling to room temperature, AcOEt (100 mL) and H₂O (100 mL) were added and the mixture was extracted with AcOEt (2×100 mL). The combined aq. layers were basified with an aq. solution of NH₃ to pH=8 and extracted with AcOEt (5×100 mL). The combined organic layers were dried (Na₂SO₄), filtered and the solvents evaporated in vacuo to yield intermediate A2 (10.6 g, 46% yield) as an oil.

The following intermediate was prepared according to the synthetic procedures described in examples A1-A2:

Example A3

Preparation of Intermediate A3

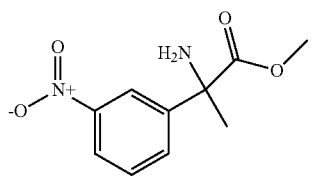

From rac-2-amino-2-(3-nitro-phenyl)-propionitrile. Flash column chromatography (silica gel; AcOEt in petroleum ether ¹/₁₀ to ¼) to yield intermediate 3 (63% yield).

Example A4

Preparation of Intermediate A4

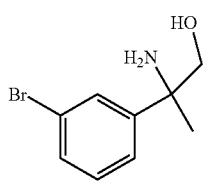

Lithium aluminium hydride (1 M in THF; 22 mL, 22 mmol) was added dropwise to a stirred solution of intermediate A2 (7.5 g, 29.1 mmol) in THF (200 mL) at −15° C. The mixture was left warming up slowly to 0° C. during 1 hour. More THF (150 mL) was added and a sat. solution of Na₂SO₄ was added dropwise until no more hydrogen was formed. Anhydrous Na₂SO₄ was added and the reaction allowed to stir overnight at room temperature. The mixture was filtered over diatomaceous earth, washed with THF and the solvent evaporated in vacuo. The crude product was purified by flash column chromatography (silica gel; 7 M solution of NH₃ in MeOH in DCM 0/100 to 3/97). The desired fractions were collected and the solvents evaporated in vacuo to yield intermediate A4 (5.70 g, 85% yield) as an oil.

Example A5

Preparation of Intermediate A5

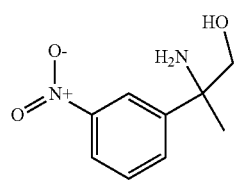

Sodium borohydride (16.3 g, 429.4 mmol) was added portionwise to a stirred solution of intermediate A3 (48.3 g, 214.7 mmol) in MeOH (500 mL). The mixture was stirred at room temperature for 10 hours. The solvent was evaporated in vacuo. The residue was basified with a sat. aq. solution of NaHCO₃ until pH=9 and extracted with AcOEt (3×200 mL). The organic layers were dried (Na₂SO₄), filtered and the solvents evaporated in vacuo to yield intermediate A5 (30.26 g, 72% yield).

Example A6

Preparation of Intermediate A6

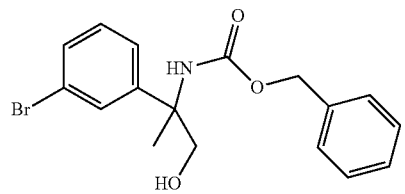 [SMILES: CC(CO)(NC(=O)OCc1ccccc1)c1cccc(Br)c1]

Benzoyl chloride (4.66 mL, 32.6 mmol) was added portionwise to a stirred solution of intermediate A4 (5 g, 21.73 mmol) in a mixture of sat. NaHCO₃ (10 mL) and THF (10 mL) at 0° C. The mixture was stirred at 0° C. for 10 min and at room temperature for 15 hours. The mixture was cooled in an ice/H₂O bath and acidified with stirring to pH=1-2 with KHSO₄. The organic layer was separated and the aq. layer was further extracted with AcOEt. The combined organic layers were separated, dried (MgSO₄), filtered and the solvents evaporated in vacuo. The crude product was purified by flash column chromatography (silica gel; AcOEt in DCM 0/100 to 20/80). The desired fractions were collected and concentrated in vacuo to yield intermediate A6 (7.8 g, 98% yield) as a colourless oil.

Example A7

Preparation of Intermediate A7

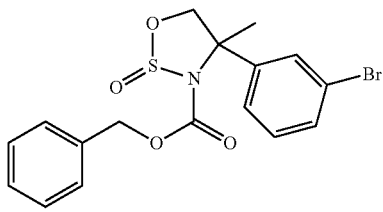 [SMILES: CC1(c2cccc(Br)c2)COS(=O)N1C(=O)OCc1ccccc1]

A solution of intermediate A6 (8 g, 21.9 mmol) in dry MeCN (20 mL) was added dropwise to a stirred solution of thionyl chloride (4.01 mL, 54.9 mmol) in dry MeCN (100 mL) cooled to −40° C. and under a nitrogen atmosphere. The reaction mixture was stirred for 60 min at −40° C. before pyridine (8.84 mL, 109.8 mmol) was added. The reaction was allowed to warm to room temperature and stirred for 14 hours. The solvent was evaporated in vacuo. The residue was treated with Et$_2$O and the solids were filtered off and the filtrate concentrated in vacuo to yield intermediate A7 (8 g, 89% yield) as a pale yellow oil. The product was used in the next reaction without further purification.

Example A8

Preparation of Intermediate A8

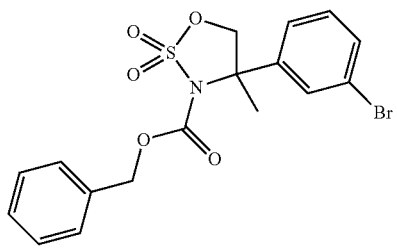 [SMILES: CC1(c2cccc(Br)c2)COS(=O)(=O)N1C(=O)OCc1ccccc1]

Ruthenium (III) chloride (41 mg, 0.195 mmol) was added to a mixture of intermediate A7 (8 g, 19.5 mmol) in MeCN/H$_2$O (1:1) (210 mL) at 0° C., followed by the addition of sodium periodate (6.26 g, 29.25 mmol). The reaction was allowed to warm to room temperature and stirred for 2 hours. The mixture was diluted with AcOEt, filtered through diatomaceous earth and washed with AcOEt. H$_2$O and AcOEt were added to the filtrate. The organic layer was separated, dried (MgSO$_4$), filtered and the solvents evaporated in vacuo. The product was purified by flash column chromatography (silica gel; DCM). The desired fractions were collected and concentrated in vacuo to yield intermediate A8 (8 g, 96% yield) as a pale yellow oil.

Example A9

Preparation of Intermediate A9

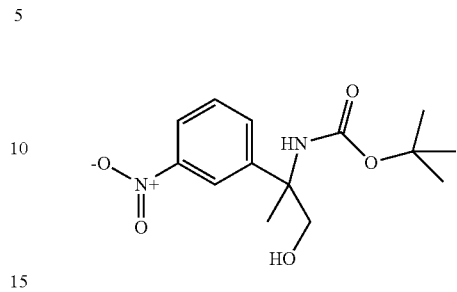

Di-tert-butyldicarbonate (10 g, 45.87 mmol) was added portionwise to a stirred solution of intermediate A5 (3 g, 15.29 mmol) in a mixture of sat. NaHCO$_3$ (50 mL) and THF (50 mL) at 0° C. The mixture was stirred at 0° C. for 10 min and at room temperature for 15 hours. The mixture was cooled in an ice/H$_2$O bath and acidified with stirring to pH=1-2 with KHSO$_4$. The organic layer was separated and the aq. layer was further extracted with AcOEt. The combined organic layers were separated, dried (MgSO$_4$), filtered and the solvents evaporated in vacuo. The crude product was purified by flash column chromatography (silica gel; AcOEt in DCM 0/100 to 100/0). The desired fractions were collected and concentrated in vacuo to yield intermediate A6 (4.5 g, 99% yield) as a pale yellow oil, that solidified upon standing.

Example A10

Preparation of Intermediate A10

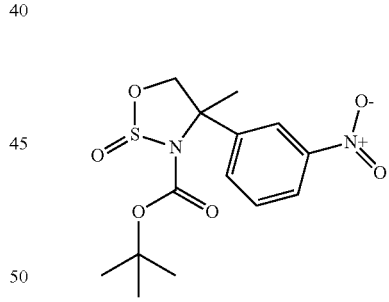

A solution of intermediate A9 (4.5 g, 15.18 mmol) in dry MeCN (20 mL) was added dropwise to a stirred solution of thionyl chloride (2.771 mL, 37.96 mmol) in dry MeCN (80 mL) cooled to −40° C. and under a nitrogen atmosphere. The reaction mixture was stirred for 30 min at −40° C. before pyridine (6.12 mL, 75.93 mmol) was added. The reaction was allowed to warm to room temperature and stirred for 18 hours. The solvent was evaporated in vacuo. The residue was treated with Et$_2$O. The solids were filtered off and the filtrate concentrated in vacuo to yield intermediate A10 (4.8 g, 92% yield) as an oil. The product was used in the next reaction without further purification.

Example A11

Preparation of Intermediate A11

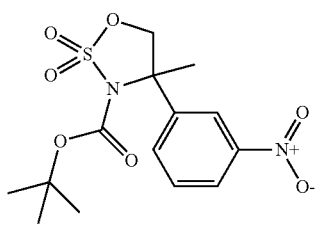 [SMILES: CC(C)(C)OC(=O)N1C(C)(c2cccc([N+](=O)[O-])c2)COS1(=O)=O]

Ruthenium (III) chloride (29.5 mg, 0.14 mmol) was added to a mixture of intermediate A10 (4.8 g, 14.02 mmol) in MeCN/H$_2$O (1:1) (100 mL) at 0° C., followed by the addition of sodium periodate (4.5 g, 21.03 mmol). The reaction was allowed to warm to room temperature and stirred for 2 hours. The mixture was diluted with AcOEt, filtered through diatomaceous earth and washed with AcOEt. H$_2$O and brine were added to the filtrate. The organic layer was separated, dried (MgSO$_4$), filtered and the solvents evaporated in vacuo. The product was purified by flash column chromatography (silica gel; DCM). The desired fractions were collected and concentrated in vacuo to yield intermediate A11 (4.9 g, 97% yield) as a pale yellow oil.

The intermediate A12 was prepared according to the synthetic procedures described in examples A9-A11:

Example A12

Preparation of Intermediate A12: (R)-[3-(tert-butyloxycarbonyl)-4-(5-bromo-2-fluorophenyl)-4-methyl-[1,1,3]oxathiazolidine-2,2-dioxide

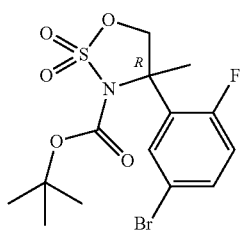

Prepared from (R)-[3-(tert-butyloxycarbonyl)-4-(5-bromo-2-fluorophenyl)-4-methyl-[1,1,3]oxathiazolidine-2-oxide (14.5 g, 36.79 mmol). Flash column chromatography (silica gel; DCM) to yield intermediate A12 as a white solid (11.6 g, 77% yield).

Example A13

Preparation of Intermediate A13

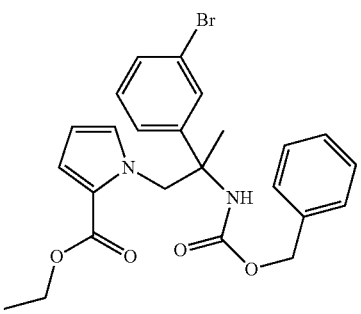 [SMILES: CCOC(=O)c1cccn1CC(C)(NC(=O)OCc1ccccc1)c1cccc(Br)c1]

Cesium carbonate (3.06 g, 9.83 mmol) was added to a mixture of intermediate A8 (2 g, 4.69 mmol) and 1H-pyrrole-2-carboxylic acid ethyl ester (763 mg, 6.1 mmol) in MeCN (16 mL) at room temperature. The mixture was heated at 130° C. for 30 min under microwave irradiation. The mixture was diluted with DCM and washed with H$_2$O. The organic phase was separated and treated with H$_2$O (10 mL) and extracted with DCM (2×10 mL). The organic layer was separated, dried (Na$_2$SO$_4$), filtered and the solvents evaporated in vacuo. The crude product was purified by flash column chromatography (silica gel; DCM). The desired fractions were collected and the solvents evaporated in vacuo to yield intermediate A13 (1.7 g, 77% yield) as a colorless oil.

Example A14

Preparation of Intermediate A14

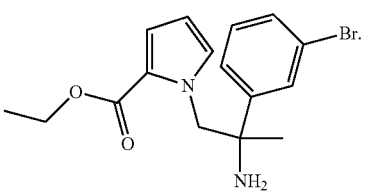 [SMILES: CCOC(=O)c1cccn1CC(C)(N)c1cccc(Br)c1]

Boron trifluoride-diethyl etherate (4.53 mL, 36.1 mmol) was added to intermediate A13 (1.7 g, 3.61 mmol) followed by ethanethiol (8.01 mL, 108.2 mmol) at 0° C. in a sealed tube. The mixture was allowed to warm to room temperature and was stirred at 60° C. for 3 hours. The solvents were evaporated in vacuo and the residue was dissolved in DCM and washed with sat. NaHCO$_3$. The organic layer was separated, dried (Na$_2$SO$_4$), filtered and the solvents evaporated in vacuo. The crude product was purified by flash column chromatography (silica gel; AcOEt in DCM, 0/100 to 50/50). The desired fractions were collected and the solvents evaporated in vacuo to yield intermediate A14 (950 mg, 78% yield) as a colorless oil.

Example A15

Preparation of Intermediate A15

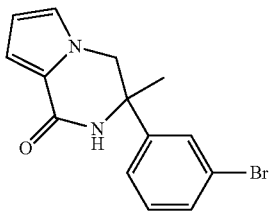 [SMILES: CC1(c2cccc(Br)c2)Cn2cccc2C(=O)N1]

Sodium methoxyde 25 wt. % in MeOH (1.284 mL, 5.36 mmol) was added to a solution of intermediate A14 (950 mg, 2.82 mmol) in MeOH (8 mL) at room temperature. The mixture was stirred at 55° C. for 18 hours. The solvent was evaporated in vacuo. The residue was treated with an aq. sat. solution of $NH_4Cl$ and extracted with DCM. The organic layer was separated, dried ($Na_2SO_4$), filtered and the solvents evaporated in vacuo to yield intermediate A15 (850 mg, 99% yield) as a white solid used in the following step without further purification.

Example A16

Preparation of Intermediate A16

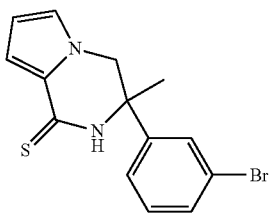 [SMILES: CC1(c2cccc(Br)c2)Cn2cccc2C(=S)N1]

Phosphoruspentasulfide (940 mg, 4.23 mmol) was added to a solution of intermediate A15 (860 mg, 2.82 mmol) in pyridine (7 mL) and the mixture was heated at 110° C. for 38 hours. The solvent was evaporated in vacuo and the crude product was purified by short column chromatography (silica gel; AcOEt in DCM 0/100 to 100/0). The desired fractions were collected and the solvents evaporated in vacuo to yield intermediate A16 (830 mg, 92% yield) as a yellow solid.

Example A17

Preparation of Intermediate A17

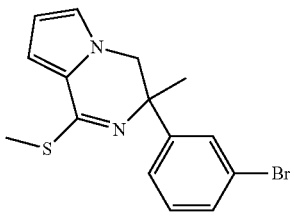 [SMILES: CSC1=NC(C)(c2cccc(Br)c2)Cn2cccc21]

Methyl iodide (0.267 mL, 4.296 mmol) and $K_2CO_3$ (0.59 g, 4.296 mmol) were added to a solution of intermediate A16 (690 mg, 2.15 mmol) in acetone (10 mL) and the mixture was stirred at room temperature for 3 hours. The solvent was evaporated in vacuo and the crude product taken up in DCM (25 mL) and $H_2O$ (25 mL). The organic layer was separated, dried ($MgSO_4$), filtered and the solvents evaporated in vacuo. The crude product was purified by flash column chromatography (silica gel; AcOEt in DCM, 0/100 to 50/50). The desired fractions were collected and the solvents evaporated in vacuo to yield intermediate A17 (700 mg, 97% yield) as a pale yellow solid.

Example A18

Preparation of Intermediate A18

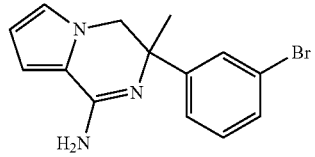 [SMILES: CC1(c2cccc(Br)c2)Cn2cccc2C(N)=N1]

$NH_4Cl$ (447 mg, 8.35 mmol) was added to a suspension of intermediate A17 (700 mg, 2.09 mmol) in a 2 M solution of $NH_3$ in EtOH (39.67 mL, 79.34 mmol) and the mixture was heated at 90° C. for 24 hours. The solvent was evaporated in vacuo and the residue suspended in a 2 M solution of $NH_3$ in EtOH (20 mL, 40 mmol). $NH_4Cl$ (447 mg, 8.35 mmol) was added and the mixture was heated at 90° C. for 2 days. The solvent was evaporated in vacuo and the residue suspended on DCM and washed with $H_2O$. The organic layer was separated, dried ($MgSO_4$), filtered and the solvents evaporated in vacuo. The product was purified by flash column chromatography (silica gel; 7 M solution of $NH_3$ in MeOH/DCM 0/100 to 20/80). The desired fractions were collected and the solvents evaporated in vacuo to yield intermediate A18 (550 mg, 86% yield) as a pale yellow solid.

Example A19

Preparation of Intermediate A19

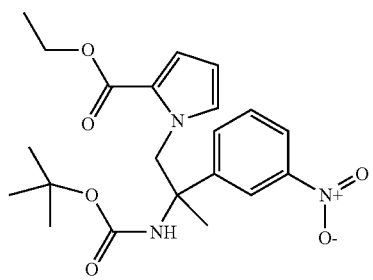 [SMILES: CCOC(=O)c1cccn1CC(C)(NC(=O)OC(C)(C)C)c1cccc([N+](=O)[O-])c1]

Cesium carbonate (2.73 g, 8.37 mmol) was added to a mixture of intermediate A11 (1.5 g, 4.186 mmol) and 1H-pyrrole-2-carboxylic acid ethyl ester (681 mg, 5.441 mmol) in MeCN (16 mL). The mixture was stirred at 130° C. for 30 min under microwave irradiation. The reaction mixture was diluted with DCM and washed with aq. HCl (1

N). The organic layer was separated, dried (Na₂SO₄), filtered and the solvents evaporated in vacuo. The crude product was purified by flash column chromatography (silica gel; DCM). The desired fractions were collected and the solvents evaporated in vacuo to yield intermediate A19 (1.5 g, 89% yield) as a colorless oil.

Example A20

Preparation of Intermediate A20

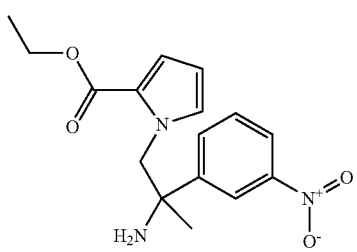 [SMILES: CCOC(=O)c1cccn1CC(C)(N)c1cccc([N+](=O)[O-])c1]

HCl (9.295 mL, 37.181 mmol, 4 M in 1,4-dioxane) was added to intermediate A19 (1.5 g, 3.718 mmol) and the mixture was stirred at room temperature for 1 hour. The solvent was evaporated in vacuo and the residue suspended in DCM and washed with an aq. sat. solution of NaHCO₃. The organic layer was separated, dried (Na₂SO₄), filtered and the solvents evaporated in vacuo to yield intermediate A20 (1.1 g, 97% yield) used in the next reaction step without further purification.

Example A21

Preparation of Intermediate A21

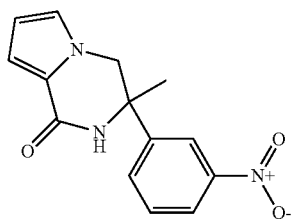 [SMILES: CC1(c2cccc([N+](=O)[O-])c2)Cn2cccc2C(=O)N1]

Sodium methoxyde 25 wt. % in MeOH (0.909 mL, 3.99 mmol) was added to a solution of intermediate A20 (1.1 g, 3.63 mmol) in MeOH (10 mL) at room temperature. The mixture was stirred at 65° C. for 18 hours. The solvent was evaporated in vacuo. The residue was treated with an aq. sat. solution of NH₄Cl and extracted with DCM. The organic layer was separated, dried (Na₂SO₄), filtered and the solvents evaporated in vacuo. The crude product was purified by flash column chromatography (silica gel; AcOEt). The desired fractions were collected, the solvents evaporated in vacuo and the resulting residue was triturated with DIPE to yield intermediate A21 (650 g, 66% yield) as a white solid.

Example A22

Preparation of Intermediate A22

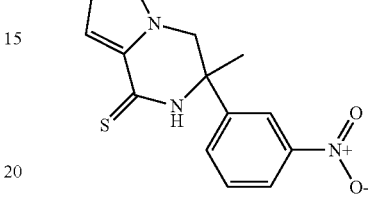

Phosphoruspentasulfide (799 mg, 3.59 mmol) was added to a solution of intermediate A21 (650 mg, 2.4 mmol) in pyridine (10 mL) and the mixture was heated at 100° C. for 18 hours. The solvent was evaporated in vacuo and the crude product was purified by short column chromatography (silica gel; AcOEt in DCM 0/100 to 100/0). The desired fractions were collected and the solvents evaporated in vacuo to yield intermediate A22 (535 mg, 78% yield) as a yellow solid.

Example A23

Preparation of Intermediate A23

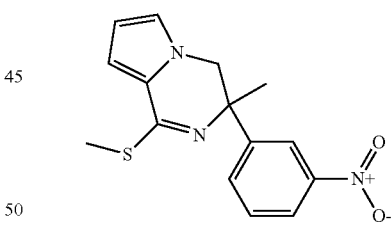

Methyl iodide (0.232 mL, 3.724 mmol) and K₂CO₃ (0.515 g, 3.724 mmol) were added to a solution of intermediate A22 (535 mg, 1.86 mmol) in acetone (10 mL) and the mixture was stirred at room temperature for 3 hours. The solvent was evaporated in vacuo and the crude product taken up in DCM (25 mL) and H₂O (25 mL). The organic layer was separated, and the aq. layer was extracted with DCM (3×25 mL). The combined organic layers were dried (MgSO₄), filtered and the solvents evaporated in vacuo. The crude product was purified by flash column chromatography (silica gel; AcOEt in DCM, 0/100 to 50/50). The desired fractions were collected and the solvents evaporated in vacuo to yield intermediate A23 (490 mg, 87% yield) as a pale yellow solid.

Example A24

Preparation of Intermediate A24

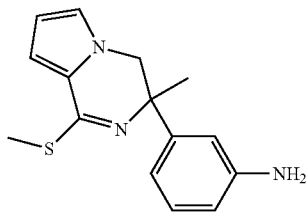 [SMILES: CSC1=NC(C)(c2cccc(N)c2)Cn2cccc21]

A solution of intermediate A23 (490 mg, 1.626 mmol) in EtOH (28 mL) was hydrogenated in a H-cube reactor (1 mL/min, 30 mm Pd/C 5% cartridge, full $H_2$ mode, room temperature, 2 cycles). Then, the solvents evaporated in vacuo. The crude product was purified by flash column chromatography (silica gel; 7 M $NH_3$ in MeOH in DCM, 0/100 to 10/90). The desired fractions were collected and the solvents evaporated in vacuo to yield intermediate A24 (100 mg, 23% yield) as a colorless oil.

Example A25

Preparation of Intermediate A25

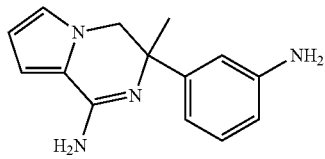 [SMILES: CC1(c2cccc(N)c2)Cn2cccc2C(N)=N1]

$NH_4Cl$ (78.8 mg, 1.474 mmol) was added to a solution of intermediate A24 (100 mg, 0.368 mmol) in a 2 M solution of $NH_3$ in EtOH (7 mL, 14 mmol) and the mixture was heated at 80° C. for 3 days. The solvent was evaporated in vacuo and the residue suspended in DCM and washed with $H_2O$. The organic layer was separated, dried ($MgSO_4$), filtered and the solvents evaporated in vacuo. The product was purified by flash column chromatography (silica gel; 7 M solution of $NH_3$ in MeOH/DCM 0/100 to 20/80). The desired fractions were collected and the solvents evaporated in vacuo to yield intermediate A25 (80 mg, 90% yield) as a pale yellow solid.

Example A26

Preparation of Intermediate A26

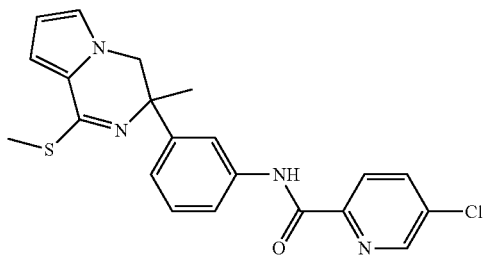 [SMILES: CSC1=NC(C)(c2cccc(NC(=O)c3ccc(Cl)cn3)c2)Cn2cccc21]

5-Chloro-pyridine-2-carboxylic acid (172 mg, 1.09 mmol) was added to a solution of 4-(4,6-dimethoxy-1,3,5-triazin-2-yl)-4-methylmorpholinium chloride (330 mg, 1.19 mmol) in MeOH (5 mL). The mixture was stirred at room temperature for 5 min. Then the mixture was cooled to 0° C. and a solution of intermediate A24 (270 mg, 0.995 mmol) in MeOH (5 mL) was added. The mixture was warmed to room temperature and stirred for 3 hours. The mixture was treated with a sat. solution of $Na_2CO_3$ and $H_2O$ and extracted with DCM. The organic layer was separated, dried ($MgSO_4$), filtered and the solvents evaporated in vacuo. The crude product was purified by flash column chromatography (silica gel; AcOEt in heptane 50/50). The desired fractions were collected and the solvents evaporated in vacuo to yield intermediate A26 (200 mg, 49% yield) as a white solid.

Example A27

Preparation of Intermediate A27

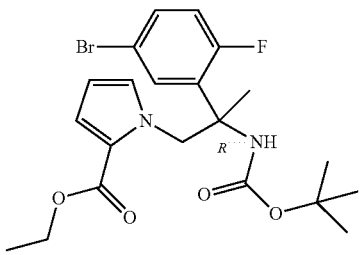

Cesium carbonate (18.27 g, 56.06 mmol) was added to a mixture of intermediate A12 (11.5 g, 28.01 mmol) and 1H-pyrrole-2-carboxylic acid ethyl ester (4.56 g, 36.44 mmol) in MeCN (40 mL) at room temperature. The mixture was stirred at room temperature for 20 min and then it was heated at 130° C. for 30 min under microwave irradiation. The mixture was diluted with DCM and washed with $H_2O$. The organic phase was dried ($Na_2SO_4$), filtered and the solvents evaporated in vacuo. The crude product was purified by flash column chromatography (silica gel; DCM/heptane, 90/10). The desired fractions were collected and the solvents evaporated in vacuo to yield intermediate A27 (10.7 g, 83% yield) as a sticky solid.

Example A28

Preparation of Intermediate A28

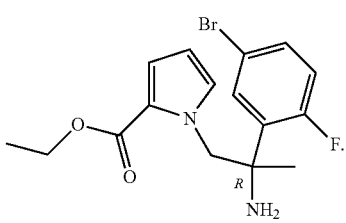

HCl (15 mL, 60 mmol, 4M in 1,4-dioxane) was added to intermediate A27 (9.5 g, 20.864 mmol) and the mixture was stirred at room temperature for 90 min. The solvent was evaporated in vacuo to yield intermediate A28 (10 g, impure, 122% yield), used in the next reaction step without further purification.

Example A29

Preparation of Intermediate A29

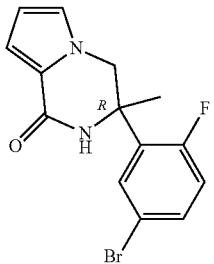

Sodium methoxide 25 wt. % in MeOH (15.714 mL, 68.93 mmol) was added to a solution of intermediate A28 (950 mg, 2.82 mmol) in MeOH (30 mL) at room temperature. The mixture was stirred at 60° C. for 18 hours. The solvent was evaporated in vacuo. The residue was treated with an aq. sat. solution of NH$_4$Cl and extracted with DCM. The organic layer was separated, dried (Na$_2$SO$_4$), filtered and the solvents evaporated in vacuo. The crude product was purified by flash column chromatography (silica gel; AcOEt in DCM 0/100 to 20/80). The desired fractions were collected and the solvents evaporated in vacuo to yield intermediate A29 (1.5 g, 18% yield) as white solid.

Example A30

Preparation of Intermediate A30

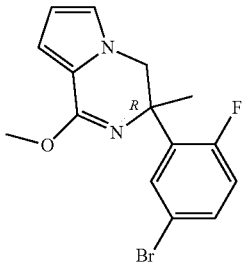

Trimethyloxonium tetrafluoroborate (2.56 g, 17.33 mmol) was added to a solution of intermediate A29 (1.4 g, 4.33 mmol) in DCM (5 mL) at room temperature. The mixture was stirred at room temperature for 4 days. The reaction mixture was diluted and then was treated with a cold aq. sat. solution of NaHCO$_3$. The organic layer was separated, dried (MgSO$_4$), filtered and the solvents evaporated in vacuo to yield intermediate A30 (910 mg, 62% yield) as an off-white solid used in the next reaction step without further purification.

Example A31

Preparation of Intermediate A31

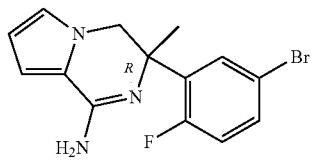

NH$_4$Cl (577 mg, 10.79 mmol) was added to a solution of intermediate A30 (910 mg, 2.7 mmol) in a 2 M solution of NH$_3$ in EtOH (5 mL, 10 mmol) and the mixture was heated at 80° C. for 36 hours into a sealed tube. The mixture was cooled to room temperature and NH$_4$Cl (432 mg, 8.1 mmol) and a 2 M solution of NH$_3$ in EtOH (5 mL, 10 mmol) were added and the mixture was heated at 80° C. for 36 hours into a sealed tube. The mixture was cooled to room temperature and NH$_4$Cl (432 mg, 8.1 mmol) and a 2 M solution of NH$_3$ in EtOH (5 mL, 10 mmol) were added and the mixture was heated at 80° C. for 48 hours into a sealed tube. The solvent was evaporated in vacuo and the residue suspended on DCM and washed with H$_2$O (4-5 mL). The organic layer was separated, dried (MgSO$_4$), filtered and the solvents evaporated in vacuo. The resulting crude product was taken up in DCM and the precipitated solid was filtered off to yield intermediate A31 (458 mg, 53% yield) as a white solid.

Example A32

Preparation of Intermediate A32

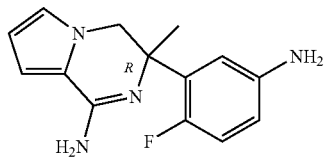

Sodium tert-butoxide (0.329 g, 3.43 mmol) was added to a mixture of intermediate A31 (0.41 g, 1.143 mmol) in toluene (8.7 mL). The mixture was stirred for 5 min and then rac-BINAP (0.213 g, 0.343 mmol) and Pd$_2$(dba)$_3$ (105 mg, 0.114 mmol), were added under nitrogen atmosphere at room temperature. The mixture was flushed with nitrogen for a few min and then benzophenone imine (0.383 mL, 2.286 mmol) was added and the mixture was stirred at 100° C. for 2 hours. After cooling to room temperature, the mixture was diluted with H$_2$O and extracted with DCM. The organic layer was separated, dried (MgSO$_4$), filtered and the solvents evaporated in vacuo. The crude product was purified by flash column chromatography (silica gel; 7 M solution of NH$_3$ in MeOH in DCM 0/100 to 50/50). The desired fractions were collected and the solvents evaporated in vacuo to yield a crude that was dissolved in HCl (6 mL, 36 mmol, 6 M in isopropyl alcohol) and the mixture was stirred at room temperature for 1 hour. The solvents evaporated in vacuo. Then the residue was taken up in DCM and isopropyl alcohol and solid NaHCO$_3$ was added and the mixture was stirred at room temperature for 2 hours. The solids were filtered off and the filtrate was evaporated in vacuo to yield intermediate A32 (400 mg, 136% yield) as a sticky oil used in the next reaction step without further purification.

Example A33

Preparation of Intermediate A33

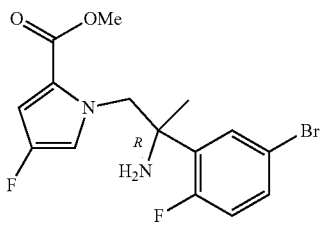

To a mixture of intermediate A12 (7.5 g, 18.281 mmol) and methyl 4-fluoro-1H-pyrrole-2-carboxylate (2.9 g, 20.263 mmol) in MeCN (150 mL) was added DBU (5.5 mL, 36.814 mmol) at room temperature. The mixture was stirred at 90° C. for 16 hours. After cooling, the solvent was mostly evaporated and the residue dissolved in DCM and washed with 0.5 M HCl. The organic layer was separated, dried (Na$_2$SO$_4$), filtered and concentrated in vacuo. The residue was dissolved in DCM (100 mL) and TFA (15 mL) was added. The mixture was stirred at room temperature for 2 hours. The solvents were evaporated in vacuo. The mixture was basified with sat. Na$_2$CO$_3$ and extracted with DCM. The organic layer was separated, dried (Na$_2$SO$_4$), filtered and the solvent evaporated in vacuo. The crude product was purified by flash column chromatography (silica gel; MeOH in DCM 0/100 to 1/99). The desired fractions were collected and concentrated in vacuo to yield intermediate A33 (4.78 g, 70% yield) as an off-white solid.

Example A34

Preparation of Intermediate A34

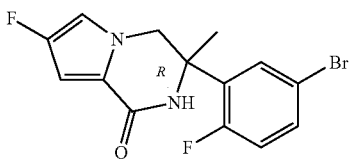

The intermediate 34 was prepared from intermediate A33 accordingly to the synthetic procedure described in example A15. Flash column chromatography (silica gel; MeOH in DCM, 0/100 to 1/99) to yield intermediate A34 as an off-white solid (4.3 g, 98% yield).

Example A35

Preparation of Intermediate A35

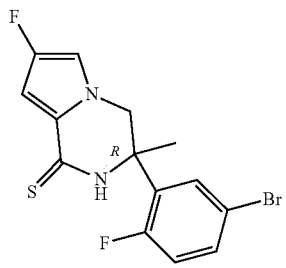

Phosphoruspentasulfide (14 g, 63.021 mmol) was added to a solution of intermediate A34 (4.3 g, 12.604 mmol) in THF (150 mL) and the mixture was heated at 70° C. for 24 hours. The reaction was filtered through celite and washed with THF. The filtrate was concentrated in vacuo. The residue was purified by flash column chromatography (silica gel; DCM). The desired fractions were collected and concentrated in vacuo to yield intermediate A35 (3.65 g, 81% yield) as a pale yellow solid.

Example A36

Preparation of Intermediate A36

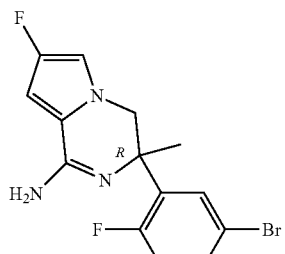

tert-Butylhydroperoxide (70%, 5.406 mL, 38 mmol) was added to a solution of intermediate 35 (1.350 g, 3.779 mmol) in 7 N NH$_3$ in MeOH (40 mL). The mixture was stirred at room temperature for 40 hours. The solvent was partially evaporated in vacuo and the residue treated with DCM and washed with a diluted Na$_2$CO$_3$ solution. The organic layer was separated, dried (Na$_2$SO$_4$), filtered and the solvents evaporated in vacuo. The crude product was purified by flash column chromatography (silica gel; 7 M solution of NH$_3$ in MeOH in DCM 0/100 to 2/98). The desired fractions were collected and concentrated in vacuo to afford intermediate A36 (990 mg, 77% yield) as a yellow solid.

Example A37

Preparation of Intermediate A37

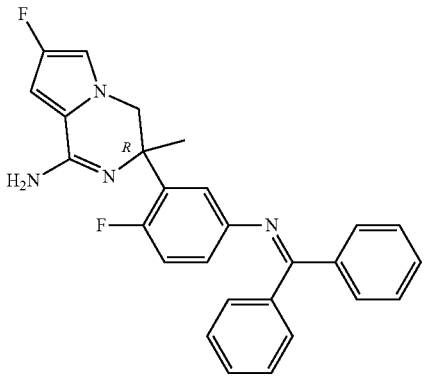

Toluene (20 mL) was added to a mixture of intermediate A36 (400 mg, 1.176 mmol), Pd$_2$(dba)$_3$ (0.108 g, 0.118 mmol), BINAP (0.22 g, 0.353 mmol) and sodium tert-butoxide (0.203 g, 2.177 mmol) under nitrogen at room temperature. The mixture was flushed with nitrogen for a few min, then benzophenone imine (0.359 mL, 2.352 mmol) was added and the mixture was stirred at 90° C. for 16 hours. After cooling, the mixture was diluted with H$_2$O and extracted with DCM. The organic layer was separated, dried (Na$_2$SO$_4$), filtered and the solvents concentrated in vacuo. The crude product was purified by flash column chromatography (silica gel; 7 N NH$_3$ in MeOH in DCM 0/100 to 1/99 to 5/95). The desired fractions were collected and concentrated in vacuo to yield intermediate A37 (440 mg, 85% yield) as a yellow foam.

Example A38

Preparation of Intermediate A38

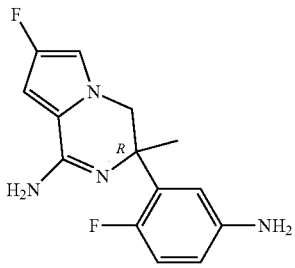

HCl (37% in H$_2$O; 500 μL, 16.182 mmol) was added to a solution of intermediate A37 (920 mg, 2.089 mmol) in isopropanol (20 mL). The mixture was stirred at room temperature for 20 min, then concentrated in vacuo and re-dissolved in 25 mL of isopropanol. Then NaHCO$_3$ was added and the mixture was stirred for 1 hour at room temperature. The mixture was filtered and the filtrate was concentrated in vacuo. The product was purified by flash column chromatography (silica gel; 7 N NH$_3$ in MeOH in DCM 1/99 to 10/90). The desired fractions were collected and concentrated in vacuo to yield intermediate A38 (470 mg, 81% yield) as an off-white foam.

Example A39

Preparation of Intermediate A39

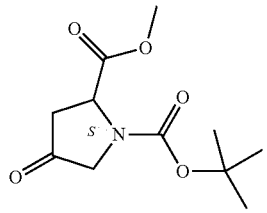

Oxalyl chloride (5.175 mL, 61.16 mmol) was added dropwise to a solution of DMSO (4.668 mL, 65.2 mmol) in DCM (103 mL) at −78° C. under nitrogen atmosphere. The mixture was stirred for 15 min at −78° C. Then N-boc-trans-4-hydroxy-1-proline methyl ester (10 g, 40.77 mmol) was added and the resulting mixture was stirred for 2 hours at −40° C. Then Et$_3$N (17 mL, 122 mmol) was added and the mixture was allowed to warm up slowly to room temperature and stirred overnight. Then the mixture was diluted with 10% citric acid solution and extracted with DCM. The organic layer was dried (Na$_2$SO$_4$), filtered and concentrated in vacuo to yield intermediate A39 (10 g) as a brown oil. The crude was used in the next step without further purification

Example A40

Preparation of Intermediate A40

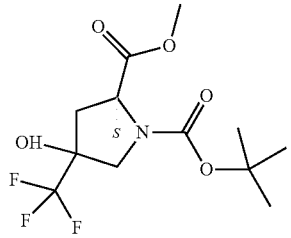

(Trifluoromethyl)trimethylsilane (8.768 g, 61.663 mmol) was added to a solution of intermediate A39 (10 g) in THF (114 mL) at 0° C., followed by the addition of TBAF (1 M in THF, 2.47 mL, 247 mmol). The reaction mixture was left to warm up at room temperature and stirred for 18 hours. The mixture was quenched with sat. aq. NH$_4$Cl. The mixture was stirred for 15 min, then TBAF (1 M in THF, 5 mL, 5 mmol) was added and the mixture was stirred for 30 min The organic layer was separated and the aq. layer was extracted with Et$_2$O. The combined organic phases were washed with H$_2$O and brine solution, then dried over Na$_2$SO$_4$, filtered and concentrated in vacuo.

The crude product was purified by flash column chromatography (silica gel; heptane in AcOEt 0/100 to 90/10). The desired fractions were collected and concentrated in vacuo to yield intermediate A40 (7.8 g, 61% yield).

Example A41

Preparation of Intermediate A41

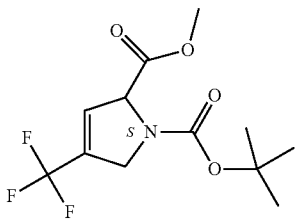

Thionyl chloride (14.352 mL, 196.633 mmol) was added to intermediate A40 (7.7 g, 24.579 mmol) in pyridine (188 mL). The mixture was stirred at 80° C. under nitrogen atmosphere for 1 hour. The mixture was quenched with $H_2O$, then extracted with $Et_2O$. The organic layer was washed with HCl 1 M, $NaHCO_3$ sat. solution, dried over $Na_2SO_4$, filtered and concentrated in vacuo. The crude product was purified by flash column chromatography (silica gel; heptane in AcOEt 0/100 to 80/20). The desired fractions were collected and concentrated in vacuo to yield intermediate A41 (4.6 g, 63% yield) as a yellow oil.

Example A42

Preparation of Intermediate A42

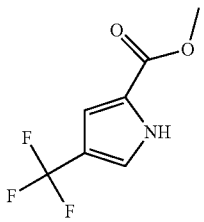

DDQ (16.607 g, 73.16 mmol) was added to intermediate A41 (7.2 g, 24.385 mmol) in dioxane (45 mL). The mixture was stirred at 85° C. for 104 hours. The mixture was filtered off and the filtrate was concentrated in vacuo. The residue was purified by flash column chromatography (silica gel; DCM in heptane 40/60). The desired fractions were collected and concentrated in vacuo to yield intermediate A42 (4 g, 85% yield) as a brownish paste.

Example A43

Preparation of Intermediate A43

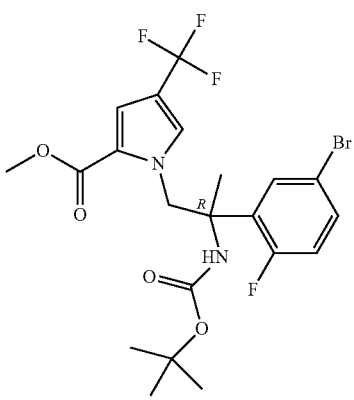

DBU (2.85 mL, 19 mmol) was added to a mixture of intermediate A12 (6.07 g, 14.84 mmol) and intermediate A42 (2 g, 10.356 mmol) in MeCN (40 mL). Then the mixture was heated at 90° C. for 18 hours. The reaction was diluted with DCM and washed with HCl 1 N solution The organic layer was separated, dried ($Na_2SO_4$), filtered and the solvent evaporated in vacuo. The product was purified by flash column chromatography (silica gel; DCM). The desired fractions were collected and concentrated in vacuo to yield intermediate A43 as a sticky solid (4.6 g, 59% yield).

Example A44

Preparation of Intermediate A44

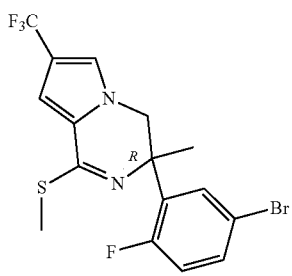

The intermediate A44 was prepared from intermediate A43 according to the synthetic procedures described in examples A20-A23. The compound was used as a crude for the subsequent reaction and the yield assumed to be quantitative.

Example A45

Preparation of Intermediate A45

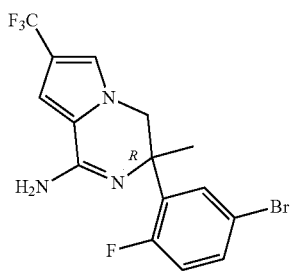

The Reaction was Set Up in Three Batches. The Total Amount of Material is Reported.

$NH_3$ (2 M in EtOH, 47 mL, 94 mmol) was added to intermediate A44 (2.3 g, 5.46 mmol) and $NH_4Cl$ (2.315 g, 43.7 mmol). The mixture was heated under microwave irradiation at 170° C. for 45 min, then concentrated in vacuo. Another 45 mL of $NH_3$ (2 M in EtOH) were added and the mixture was heated under microwave irradiation at 170° C. for 45 min. The mixture was filtered and concentrated in vacuo. The crude was purified by flash column chromatography (silica gel; MeOH in DCM 0/100 to 3/97). The desired fractions were collected and concentrated in vacuo to yield intermediate A45 (2.1 g, 99% yield).

The intermediate A46 was prepared according to the synthetic procedures described in examples A37-A38:

Example A46

Preparation of Intermediate A46

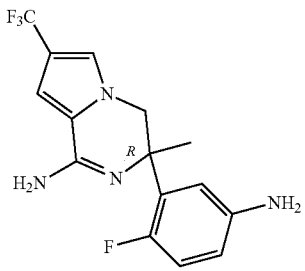

Prepared from intermediate A45. Compound precipitated from the crude reaction mixture using DCM (89% yield).

The intermediate A47 was prepared according to the synthetic procedure described in examples A9-A11:

Example A47

Preparation of Intermediate A47

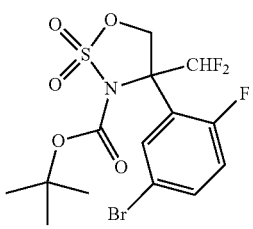

Prepared from carbamic acid, N-[1-(5-bromo-2-fluorophenyl)-2,2-difluoro-1-(hydroxymethyl)ethyl]-, 1,1-dimethylethyl ester. The crude product was triturated with heptane and filtered. The grey solid was dissolved in DCM and purified by column chromatography (silica gel; DCM). The desired fractions were collected and concentrated in vacuo to yield intermediate A47 (78% yield) as a white solid.

Example A48

Preparation of Intermediate A48

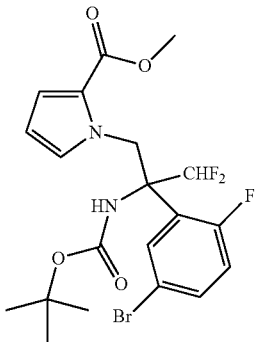 [SMILES: COC(=O)c1cccn1CC(NC(=O)OC(C)(C)C)(c1cc(Br)ccc1F)C(F)F]

NaH (60% dispersion in mineral oil, 269 mg, 6.723 mmol) was added to a mixture of methyl 2-pyrrolecarboxylate (841 mg, 6.723 mmol) in DMF (20 mL) at 0° C. under nitrogen. Then the mixture was stirred for 10 min at 0° C. and then a solution of intermediate A47 (2 g, 4.482 mmol) in DMF (10 mL) was added and the mixture was stirred at room temperature for 20 hours. The reaction was quenched with $NH_4Cl$ sat. and extracted with AcOEt. The organic layer was separated, dried ($MgSO_4$), filtered and the solvent evaporated in vacuo to yield intermediate A48 (2.2 g, 100% yield) as an oil, which was used in next step without further purification.

The intermediate A49 was prepared according to the synthetic procedure described in example A20:

Example A49

Preparation of Intermediate A49

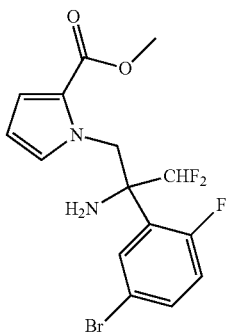 [SMILES: COC(=O)c1cccn1CC(N)(c1cc(Br)ccc1F)C(F)F]

Prepared from intermediate A48. Flash column chromatography (silica gel; AcOEt in heptane 0/100 to 15/85). to yield intermediate A49 (100% yield).

Example A50

Preparation of Intermediate A50

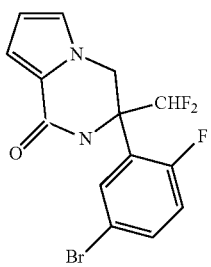

Trimethylaluminum (2 M in toluene; 4.47 mL, 8.9 mmol) was added to a stirred mixture of intermediate A49 (1.75 g, 4.47 mmol) in THF (20 mL) at 0° C. in a sealed tube. The mixture was stirred at 100° C. for 2 hours. The mixture was cooled to room temperature, poured into a flask, cooled at 0° C. and quenched with sodium sulfate decahydrate. The mixture was stirred for 15 min, then filtered and the filtrates were evaporated in vacuo to yield intermediate A49 (1.657 g, 103% yield) as a solid, which was used in next step without further purifications.

The intermediate A51 was prepared according to the synthetic procedure described in example A16:

Example A51

Preparation of Intermediate A51

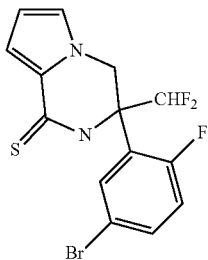 [SMILES: Fc1ccc(Br)cc1C1(C(F)F)Cn2cccc2C(=S)N1]

Prepared from intermediate 50. Flash column chromatography (silica gel; MeOH in DCM 0/100 to 05/95) to yield intermediate A51 (52% yield) as a pale yellow solid.

Example A52

Preparation of Intermediate A52

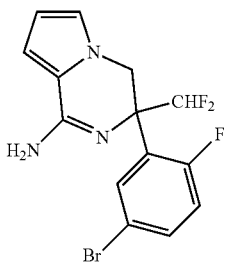

NH$_3$ aq. solution (7 mL) was added to a solution of intermediate A51 (700 mg, 1.866 mmol) in 7 N NH$_3$ in MeOH (7 mL) and the mixture was heated at 90° C. in a sealed tube for 21 hours. Then the solvent was evaporated and more aq. NH$_3$ and 7 N NH$_3$ in MeOH were added. The mixture was stirred at 90° C. for 24 hours. The solvent was evaporated in vacuo. The crude product was purified by flash column chromatography (silica gel; MeOH in DCM 0/100 to 03/97). The desired fractions were collected and concentrated in vacuo to yield intermediate A52 (464 mg, 69% yield).

The intermediate A53 was prepared according to the synthetic procedure described in examples A37-A38:

Example A53

Preparation of Intermediate A53

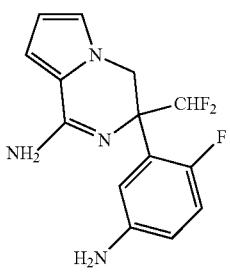 [SMILES: NC1=NC(c2cc(N)ccc2F)(C(F)F)Cn2cccc21]

Prepared from intermediate A52. Flash column chromatography (silica gel; 7 N NH$_3$ in MeOH in DCM 0/100 to 10/90). The desired fractions were collected and concentrated in vacuo to yield intermediate A53 (69% yield).

Example A54

Preparation of Intermediate A54

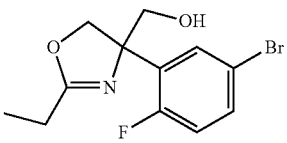 [SMILES: CCC1=NC(CO)(c2cc(Br)ccc2F)CO1]

A drop of AcOH was added to a stirred solution of 2-amino-2-(5-bromo-2-fluorophenyl)-1,3-propanediol (4.2 g, 15.9 mmol) and triethyl orthopropionate (3.52 mL, 17.5 mmol) in DCE (80 mL) at room temperature. The mixture was heated at 80° C. for 90 min, and then treated with aq. Na$_2$CO$_3$ sat. and extracted with DCM. The organic layer was separated, dried (MgSO$_4$), filtered and the solvent evaporated in vacuo to afford an oil (4.63 g), which was used in next step without further purification.

Example A55

Preparation of Intermediate A55

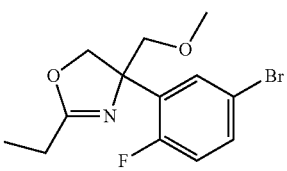 [SMILES: CCC1=NC(COC)(c2cc(Br)ccc2F)CO1]

NaH (60% dispersion in mineral oil, 735 mg, 18.4 mmol) was added to a solution of intermediate A54 (4.63 g, 15.3 mmol) in DMF (40 mL) at 0° C. under nitrogen. The mixture was stirred for 10 min at 0° C., then methyl iodide (1.91 mL, 30.65 mmol) was added. The mixture was stirred at room temperature for 90 min, then quenched with aq. sat. NH$_4$Cl and extracted with heptane. The organic layer was separated, dried (MgSO$_4$), filtered and the solvent evaporated in vacuo to yield intermediate A55 as an oil (4.73 g), which was used in next step without further purification.

Example A56

Preparation of Intermediate A56

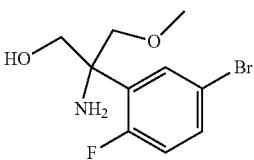

A solution of intermediate A55 (4.95 g, 15.7 mmol) in HCl (6 M in H₂O, 40 mL) was heated at 100° C. for 1 hour. The solvent was then evaporated to give intermediate A56 as an oil (4.3 g), which was used in next step without further purification.

The intermediate A57 was prepared according to the synthetic procedures described in examples A9-A11, A43, A20, A50, A35, A36:

Example A57

Preparation of Intermediate A57

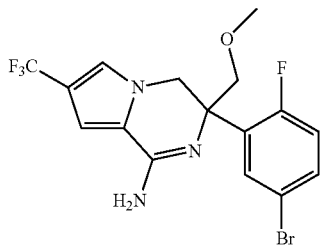 [SMILES: COCC1(c2cc(Br)ccc2F)Cn2cc(C(F)(F)F)cc2C(N)=N1]

Prepared from intermediate A56. Flash column chromatography (silica gel; 7 N NH₃ in MeOH in DCM 0/100 to 5/95) to yield intermediate A57 (68% yield).

Example A58

Preparation of Intermediate A58

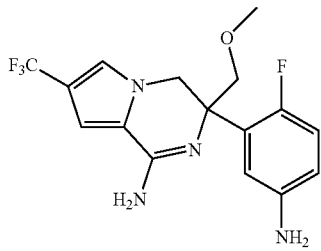 [SMILES: COCC1(c2cc(N)ccc2F)Cn2cc(C(F)(F)F)cc2C(N)=N1]

Copper iodide (84 mg, 0.41 mmol) was added to a suspension of intermediate A57 (617 mg, 1.47 mmol), sodium azide (242 mg, 3.67 mmol), N,N'-dimethylethylendiamine (142 μL, 1.32 mmol) and Na₂CO₃ (447 mg, 4.41 mmol) in DMSO (13 mL) and the reaction was degassed. The mixture was heated at 110° C. for 25 hours, then quenched with 1 M HCl and the water layer basified with NH₄OH and extracted with AcOEt (3×). The combined organic layers were dried (MgSO₄), filtered and concentrated. The crude product was purified by flash column chromatography (silica; 7 N solution of NH₃ in MeOH in DCM 0/100 to 5/95). The desired fractions were collected and concentrated in vacuo to yield intermediate A58 (480 mg, 92% yield).

Preparation of the Final Compounds

Example B1

Preparation of compound 1: rac-3-methyl-3-(3-pyrimidin-5-yl-phenyl)-3,4-dihydro-pyrrolo[1,2-a]pyrazin-1-ylamine

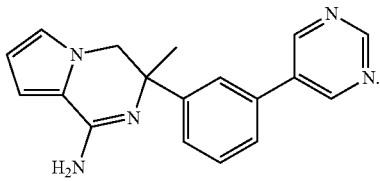 [SMILES: CC1(c2cccc(-c3cncnc3)c2)Cn2cccc2C(N)=N1]

trifluoroacetate salt

Pd(PPh₃)₄ (57 mg, 0.049 mmol) was added to a stirred suspension of intermediate A18 (300 mg, 0.99 mmol), pyrimidine-5-boronic acid (367 mg, 2.96 mmol) and K₂CO₃ (409 mg, 2.96 mmol) in a mixture of 1,4-dioxane (4 mL) and EtOH (0.4 mL) in a sealed tube. The mixture was heated at 150° C. for 30 min under microwave irradiation. After cooling to room temperature, the mixture was diluted with H₂O and extracted with DCM. The organic layer was separated, dried (MgSO₄), filtered and the solvents were evaporated in vacuo. The crude product was purified by short column chromatography (silica gel; 7 M solution of NH₃ in MeOH/DCM 0/100 to 3/97). The desired fractions were collected and concentrated in vacuo to give a solid that was triturated with Et₂O, sonicated, filtered and dried in vacuo at 50° C. to yield a solid that was further purified by reverse phase HPLC (Gradient from 80% of a 0.1% TFA solution in H₂O, 20% MeCN to 0% of a 0.1% TFA solution in H₂O, 100% MeCN) to yield compound 1 (90.3 mg, 22% yield) as a solid. ¹H NMR (400 MHz, DMSO-d₆) δ ppm 1.74 (s, 3H), 4.40 (d, J=13.6 Hz, 1H), 5.03 (d, J=13.4 Hz, 1H), 6.26 (dd, J=4.2, 2.5 Hz, 1H), 7.19 (dd, J=4.2, 1.4 Hz, 1H), 7.31 (t, J=1.6 Hz, 1H), 7.45 (br. d, J=8.1 Hz, 1H), 7.54 (t, J=7.9 Hz, 1H), 7.75 (br. d, J=7.9 Hz, 1H), 7.91 (br. s, 1H), 8.38 (br. s., 1H), 9.16 (s, 2H), 9.21 (br. s, 1H), 9.22 (s, 1H), 10.23 (br. s, 1H).

Example B2

Preparation of compound 2: rac-3-(3',5'-dichloro-biphenyl-3-yl)-3-methyl-3,4-dihydro-pyrrolo[1,2-a]pyrazin-1-ylamine

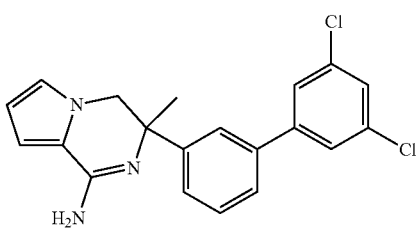 [SMILES: CC1(c2cccc(-c3cc(Cl)cc(Cl)c3)c2)Cn2cccc2C(N)=N1]

Pd(PPh₃)₄ (30.4 mg, 0.026 mmol) was added to a stirred suspension of intermediate A18 (160 mg, 0.526 mmol), 2,3-dichlorophenyl-boronic acid (120.4 mg, 0.631 mmol) and K₂CO₃ (218 mg, 1.58 mmol) in a mixture of 1,4-dioxane (4 mL) and EtOH (0.4 mL) in a sealed tube. The mixture was heated at 60° C. for 18 hours. After cooling to room temperature, the mixture was diluted with H$_2$O and NH$_4$Cl (aq. sat. solution) and extracted with DCM. The organic layer was separated, dried (Na$_2$SO$_4$), filtered and the solvents were evaporated in vacuo. The crude product was purified by short column chromatography (MeOH in DCM 0/100 to 3/97). The desired fractions were collected and concentrated in vacuo to give a solid that was triturated with DIPE, filtered and dried in vacuo at 50° C. to yield compound 2 (136 mg, 70% yield) as a solid. $^1$H NMR (500 MHz, CDCl$_3$) δ ppm 1.56 (s, 3H), 4.11 (br. s, 2H), 4.05 (d, J=12.4 Hz, 1H), 4.10 (d, J=12.7 Hz, 1H), 6.18 (dd, J=3.8, 2.6 Hz, 1H), 6.43 (dd, J=3.8, 1.4 Hz, 1H), 6.75 (dd, J=2.3, 1.4 Hz, 1H), 7.32 (t, J=1.7 Hz, 1H), 7.36-7.42 (m, 2H), 7.43 (d, J=1.7 Hz, 2H), 7.53 (dt, J=6.9, 1.9 Hz, 1H), 7.65-7.71 (m, 1H).

Example B3

Preparation of compound 3: rac-5-chloro-pyridine-2-carboxylic acid[3-(1-amino-3-methyl-3,4-dihydro-pyrrolo[1,2-a]pyrazin-3-ye-phenyl]-amide

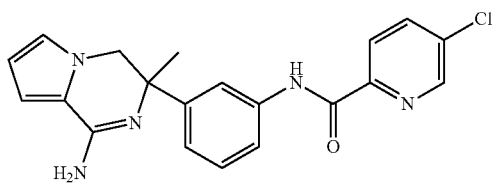 [SMILES: CC1(c2cccc(NC(=O)c3ccc(Cl)cn3)c2)Cn2cccc2C(N)=N1]

NH$_4$Cl (94 mg, 1.75 mmol) was added to a suspension of intermediate A26 (180 mg, 0.44 mmol) in a 2 M solution of NH$_3$ in EtOH (8.23 mL) and the mixture was heated at 80° C. for 6 days. The solvent was evaporated in vacuo and the residue suspended in DCM and washed with H$_2$O. The organic layer was separated, dried (MgSO$_4$), filtered and the solvents evaporated in vacuo. The product was purified by flash column chromatography (silica gel; 7 M solution of NH$_3$ in MeOH/DCM 0/100 to 10/90). The desired fractions were collected and the solvents evaporated in vacuo to yield compound 3 (28 mg, 17% yield) as a white solid. $^1$H NMR (500 MHz, CDCl$_3$) δ ppm 1.56 (s, 3H), 2.96 (br. s., 2H), 4.06 (d, J=12.7 Hz, 1H), 4.14 (d, J=13.3 Hz, 1H), 6.17 (dd, J=3.8, 2.6 Hz, 1H), 6.46 (dd, J=3.8, 1.2 Hz, 1H), 6.75 (dd, J=2.3, 1.4 Hz, 1H), 7.30 (br. d, J=7.8 Hz, 1H), 7.35 (t, J=8.1 Hz, 1H), 7.68-7.73 (m, 1H), 7.88 (dd, J=8.4, 2.3 Hz, 1H), 7.91 (t, J=1.7 Hz, 1H), 8.25 (d, J=8.4 Hz, 1H), 8.57 (d, J=2.0 Hz, 1H), 9.86 (br. s., 1H).

Example B4

Preparation of compound 4: rac-5-methoxy-pyrazine-2-carboxylic acid [3-(1-amino-3-methyl-3,4-dihydro-pyrrolo[1,2-a]pyrazin-3-ye-phenyl]-amide

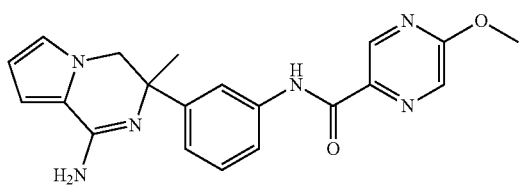 [SMILES: COc1cnc(C(=O)Nc2cccc(C3(C)Cn4cccc4C(N)=N3)c2)cn1]

5-Methoxy-pyrazine-2-carboxylic acid (56.4 mg, 0.36 mmol) was added to a solution of 4-(4,6-dimethoxy-1,3,5-triazin-2-yl)-4-methylmorpholinium chloride (111 mg, 0.4 mmol) in MeOH (4 mL). The mixture was stirred at room temperature for 5 min. Then the mixture was cooled to 0° C. and a solution of intermediate A25 (80 mg, 0.33 mmol) in MeOH (2 mL) was added. The mixture was warmed to room temperature and stirred for 3 hours. The mixture was treated with a sat. solution of Na$_2$CO$_3$ and H$_2$O and extracted with DCM. The organic layer was separated, dried (Na$_2$SO$_4$), filtered and the solvents evaporated in vacuo. The crude product was triturated with Et$_2$O and then was purified by flash column chromatography (silica gel; AcOEt in heptane 50/50). The desired fractions were collected and the solvents evaporated in vacuo to yield compound 4 (65 mg, 52% yield) as a white solid. $^1$H NMR (500 MHz, DMSO-d$_6$) δ ppm 1.36 (s, 3H), 4.03 (s, 3H), 3.99-4.11 (m, 2H), 6.06 (br. s., 2H), 6.02 (dd, J=3.5, 2.6 Hz, 1H), 6.52 (dd, J=3.5, 1.2 Hz, 1H), 6.87 (t, J=1.7 Hz, 1H), 7.26 (t, J=7.8 Hz, 1H), 7.28-7.33 (m, 1H), 7.72 (dt, J=7.5, 1.7 Hz, 1H), 8.02 (br. s, 1H), 8.43 (d, J=1.2 Hz, 1H), 8.90 (d, J=1.2 Hz, 1H), 10.33 (br. s., 1H).

Example B5

Preparation of compound 5: (R)-5-chloro-pyridine-2-carboxylic acid [3-(1-amino-3-methyl-3,4-dihydro-pyrrolo[1,2-a]pyrazin-3-yl)-4-fluoro-phenyl]-amide

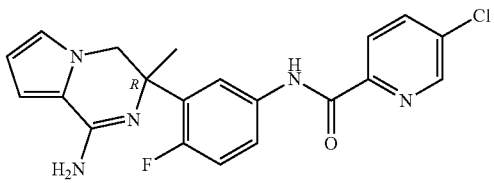

5-Chloro-pyridine-2-carboxylic acid (122 mg, 0.774 mmol) was added to a solution of 4-(4,6-dimethoxy-1,3,5-triazin-2-yl)-4-methylmorpholinium chloride (214 mg, 0.774 mmol) in MeOH (4 mL). The mixture was stirred at room temperature for 5 min. Then the mixture was cooled to 0° C. and a solution of intermediate A32 (200 mg, 0.774 mmol) in MeOH (3 mL) was added. The mixture was warmed to room temperature and stirred for 90 min. The mixture was concentrated in vacuo in a cold bath, and then it was treated with a sat. solution of Na$_2$CO$_3$ and H$_2$O and extracted with DCM. The organic layer was separated, dried (MgSO$_4$), filtered and the solvents evaporated in vacuo. The crude product was purified by flash column chromatography (silica gel; 7 N NH$_3$ in MeOH in DCM 0/100 to 2/98). The desired fractions were collected and the solvents evaporated in vacuo to yield a residue that was triturated with Et$_2$O to yield compound 5 (65 mg, 21% yield) as a white solid. $^1$H NMR (500 MHz, CDCl$_3$) δ ppm 1.56 (s, 3H), 4.20 (br. d, J=12.7 Hz, 1H), 4.28 (br. d, J=12.4 Hz, 1H), 4.59 (br. s., 2H), 6.16 (dd, J=3.5, 2.6 Hz, 1H), 6.43 (br. d, J=2.6 Hz, 1H), 6.74-6.78 (m, 1H), 7.06 (dd, J=11.7, 8.8 Hz, 1H), 7.79 (dd, J=6.9, 2.6 Hz, 1H), 7.87 (dd, J=8.4, 2.3 Hz, 1H), 8.02 (ddd, J=9.0, 4.0, 3.2 Hz, 1H), 8.23 (d, J=8.4 Hz, 1H), 8.56 (d, J=2.0 Hz, 1H), 9.82 (br. s., 1H).

Example B6

Preparation of compound 6: (R)-5-Cyano-pyridine-2-carboxylic acid [3-(1-amino-3-methyl-3,4-dihydro-pyrrolo[1,2-a]pyrazin-3-yl)-4-fluoro-phenyl]-amide

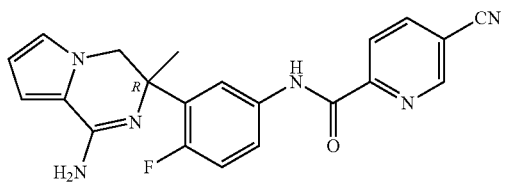

5-Cyano-pyridine-2-carboxylic acid (115 mg, 0.774 mmol) was added to a solution of 4-(4,6-dimethoxy-1,3,5-triazin-2-yl)-4-methylmorpholinium chloride (214 mg, 0.774 mmol) in MeOH. The mixture was stirred at room temperature for 5 min. Then, the mixture was cooled to 0° C. and a solution of intermediate A32 (200 mg, 0.774 mmol) in MeOH was added (total amount of MeOH 4 mL). The mixture was warmed to room temperature and stirred for 3 hours. The mixture was concentrated in vacuo in a cold bath, and then it was treated with a sat. solution of $Na_2CO_3$ and $H_2O$ and extracted with DCM. The organic layer was separated, dried ($MgSO_4$), filtered and the solvents evaporated in vacuo. The crude product was purified by flash column chromatography (silica gel; 7 N $NH_3$ in MeOH in DCM 0/100 to 2/98). The desired fractions were collected and the solvents evaporated in vacuo to yield a residue that was triturated with $Et_2O$ to yield compound 7 (110 mg, 37% yield) as a white solid. $^1$H NMR (500 MHz, $CDCl_3$) δ ppm 1.57 (s, 3H), 4.21 (br. d, J=12.1 Hz, 1H), 4.28 (br. d, J=12.7 Hz, 1H), 4.37 (br. s., 1H), 6.16 (dd, J=3.8, 2.6 Hz, 1H), 6.43 (dd, J=3.8, 1.2 Hz, 1H), 6.77 (dd, J=2.5, 1.3 Hz, 1H), 7.08 (dd, J=11.7, 8.8 Hz, 1H), 7.83 (dd, J=6.9, 2.9 Hz, 1H), 8.01 (ddd, J=8.7, 4.0, 2.9 Hz, 1H), 8.18 (dd, J=8.1, 2.0 Hz, 1H), 8.40 (dd, J=8.1, 0.6 Hz, 1H), 8.85 (br. d, J=1.2 Hz, 1H), 9.85 (br. s., 1H).

Example B7

Preparation of compound 7: (R)-5-Fluoro-pyridine-2-carboxylic acid [3-(1-amino-7-fluoro-3-methyl-3,4-dihydro-pyrrolo[1,2-a]pyrazin-3-yl)-4-fluoro-phenyl]-amide

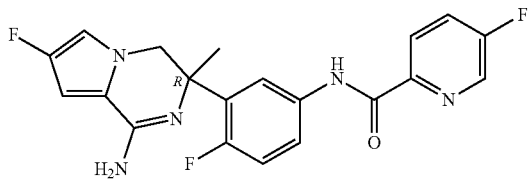

5-Fluoro-pyridine-2-carboxylic acid (123 mg, 0.869 mmol) was added to a solution of 4-(4,6-dimethoxy-1,3,5-triazin-2-yl)-4-methylmorpholinium chloride (240 mg, 0.869 mmol) in MeOH (4 mL). The mixture was stirred at room temperature for 5 min. Then, the mixture was cooled to 0° C. and a solution of intermediate A38 (200 mg, 0.724 mmol) in MeOH (2 mL) was added. The mixture was warmed to room temperature and stirred for 2 hours. The mixture was treated with a sat. solution of $Na_2CO_3$ and $H_2O$ and extracted with DCM. The organic layer was separated, dried ($Na_2SO_4$), filtered and the solvents evaporated in vacuo. The crude product was purified by flash column chromatography (silica gel; 7 N $NH_3$ in MeOH in DCM 0/100 to 4/96). The desired fractions were collected and the solvents evaporated in vacuo to yield a residue that was triturated with heptane to yield compound 8 (196 mg, 68% yield) as a white solid. $^1$H NMR (400 MHz, DMSO-$d_6$) δ ppm 1.41 (s, 3H), 3.98 (br. d, J=12.7 Hz, 1H), 4.10 (br. d, J=12.5 Hz, 1H), 6.16 (br. s., 2H), 6.41 (d, J=1.6 Hz, 1H), 6.94 (dd, J=3.4, 2.0 Hz, 1H), 7.16 (dd, J=12.0, 8.8 Hz, 1H), 7.75 (ddd, J=8.8, 4.2, 2.8 Hz, 1H), 7.97 (td, J=8.7, 2.8 Hz, 1H), 8.11 (dd, J=7.5, 2.7 Hz, 1H), 8.21 (dd, J=8.8, 4.6 Hz, 1H), 8.73 (d, J=2.8 Hz, 1H), 10.51 (br. s, 1H).

Example B8

Preparation of compound 8: (R)-5-methoxy-pyrazine-2-carboxylic acid [3-(1-amino-7-fluoro-3-methyl-3,4-dihydro-pyrrolo[1,2-a]pyrazin-3-yl)-4-fluoro-phenyl]-amide

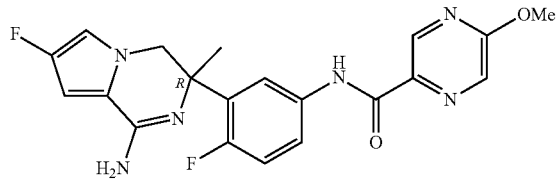

5-Methoxy-pyrazine-2-carboxylic acid (134 mg, 0.869 mmol) was added to a solution of 4-(4,6-dimethoxy-1,3,5-triazin-2-yl)-4-methylmorpholinium chloride (240 mg, 0.869 mmol) in MeOH (4 mL). The mixture was stirred at room temperature for 5 min. Then, the mixture was cooled to 0° C. and a solution of intermediate A38 (200 mg, 0.724 mmol) in MeOH (2 mL) was added. The mixture was warmed to room temperature and stirred for 2 hours. The mixture was treated with a sat. solution of $Na_2CO_3$ and $H_2O$ and extracted with DCM. The organic layer was separated, dried ($Na_2SO_4$), filtered and the solvents evaporated in vacuo. The crude product was purified by flash column chromatography (silica gel; 7 N $NH_3$ in MeOH in DCM 0/100 to 4/96). The desired fractions were collected and the solvents evaporated in vacuo to yield a residue that was triturated with heptane to yield compound 8 (213 mg, 71% yield) as a white solid. $^1$H NMR (400 MHz, DMSO-$d_6$) δ ppm 1.41 (s, 3H), 3.97 (br. d, J=12.9 Hz, 1H), 4.02 (s, 3H), 4.09 (br. d, J=12.5 Hz, 1H), 6.12 (br. s., 2H), 6.40 (d, J=1.8 Hz, 1H), 6.93 (dd, J=3.2, 1.8 Hz, 1H), 7.15 (dd, J=12.0, 8.8 Hz, 1H), 7.72 (ddd, J=8.8, 4.2, 3.0 Hz, 1H), 8.12 (dd, J=7.4, 2.8 Hz, 1H), 8.41 (d, J=1.4 Hz, 1H), 8.87 (d, J=1.2 Hz, 1H), 10.40 (br. s, 1H).

Example B9

Preparation of compound 9: (R)-5-cyano-pyridine-2-carboxylic acid [3-(1-amino-3-methyl-7-trifluoromethyl-3,4-dihydro-pyrrolo[1,2-a]pyrazin-3-ye-4-fluoro-phenyl]-amide

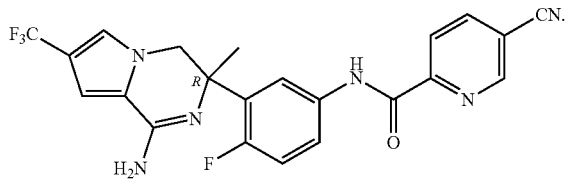

trifluoroacetate salt

5-Cyano-pyridine-2-carboxylic acid (82 mg, 0.551 mmol) was added to a solution of 4-(4,6-dimethoxy-1,3,5-triazin-2-yl)-4-methylmorpholinium chloride (168 mg, 0.606 mmol) in MeOH (3 mL). The mixture was stirred at room temperature for 5 min. Then, the mixture was cooled to 0° C. and a solution of intermediate A46 (200 mg, 0.551 mmol) in MeOH (2 mL) was added. The mixture was warmed to room temperature and stirred for 18 hours. The mixture was concentrated in vacuo in a cold bath, and then it was treated with sat. $Na_2CO_3$ solution and extracted with DCM. The organic layer was separated, dried ($Na_2SO_4$), filtered and concentrated in vacuo.

The crude product was purified by flash column chromatography (silica gel; MeOH in DCM 0/100 to 4/96) The desired fractions were collected and the solvent evaporated in vacuo. The compound was triturated with $Et_2O$ to yield a mixture that was repurified by flash column chromatography (silica gel; MeOH in DCM 0/100 to 4/96) The desired fractions were collected and the solvent evaporated in vacuo to yield an impure fraction, that was purified by RP HPLC on (C18 Sunfire 30×100 Sum). Mobile phase (Gradient from 80% of a 0.1% TFA solution in $H_2O$, 20% MeCN to 0% of a 0.1% TFA solution in $H_2O$, 100% MeCN), yielding of compound 9 (121.3 mg, 39% yield) as a white solid. $^1$H NMR (500 MHz, DMSO-$d_6$) δ ppm 1.79 (s, 3H), 4.50 (br. d, J=13.6 Hz, 1H), 4.92 (br. d, J=13.3 Hz, 1H), 7.31 (dd, J=11.8, 8.7 Hz, 1H), 7.51 (br. s, 1H), 7.86-7.93 (m, 2H), 7.95 (br. s, 1H), 8.25 (d, J=8.1 Hz, 1H), 8.58 (dd, J=8.4, 2.0 Hz, 1H), 8.87 (br. s., 1H), 9.20 (d, J=1.2 Hz, 1H), 9.55 (br. s., 1H), 10.67 (br. s., 1H), 10.99 (br. s, 1H).

Example B10

Preparation of compound 10: (R)-1-difluoromethyl-1H-pyrazole-3-carboxylic acid [3-(1-amino-3-methyl-7-trifluoromethyl-3,4-dihydro-pyrrolo[1,2-a]pyrazin-3-ye-4-fluorophenyl]-amide

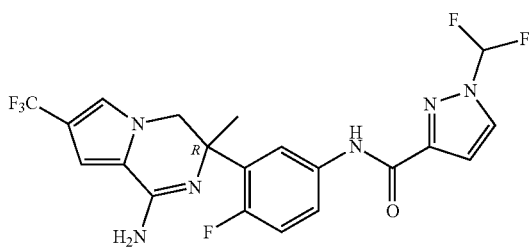

1-Difluoromethyl-1H-pyrazole-3-carboxylic acid (31 mg, 0.193 mmol) was added to a solution of 4-(4,6-dimethoxy-1,3,5-triazin-2-yl)-4-methylmorpholinium chloride (59 mg, 0.212 mmol) in MeOH (3 mL). The mixture was stirred for 5 min at room temperature. The mixture was cooled to 0° C. and intermediate A46 (70 mg, 0.193 mmol, previously treated with $NH_3$ in MeOH to generate the free base) in MeOH (2 mL) was added. Then the mixture was stirred at room temperature for 18 hours.

The mixture was concentrated in vacuo in a cold bath, and then it was treated with sat. $Na_2CO_3$ solution and extracted with DCM. The organic layer was separated, dried ($Na_2SO_4$), filtered and concentrated in vacuo. The crude product was purified by flash column chromatography (silica gel; MeOH in DCM 0/100 to 4/96) The desired fractions were collected and the solvent evaporated in vacuo. The compound was triturated with $Et_2O$, to yield compound 10 (56 mg, 62% yield) as a white solid. $^1$H NMR (500 MHz, DMSO-$d_6$) δ ppm 1.40 (s, 3H), 4.13 (br. d, J=13.0 Hz, 1H), 4.29 (br. d, J=12.7 Hz, 1H), 6.25 (br. s., 2H), 6.87 (br. s, 1H), 7.01 (d, J=2.3 Hz, 1H), 7.16 (dd, J=11.8, 9.0 Hz, 1H), 7.59 (br. s, 1H), 7.63-7.69 (m, 1H), 7.92 (t, J=58.7 Hz, 1H), 8.05-8.10 (m, 1H), 8.41 (d, J=2.3 Hz, 1H), 10.34 (s, 1H).

Example B11

Preparation of compound 11: rac-5-methoxy-pyridine-2-carboxylic acid [3-(1-amino-3-difluoromethyl-3,4-dihydro-pyrrolo[1,2-a]pyrazin-3-yl)-4-fluoro-phenyl]-amide, compound 12: (R*)-5-methoxy-pyridine-2-carboxylic acid [3-(1-amino-3-difluoromethyl-3,4-dihydro-pyrrolo[1,2-a]pyrazin-3-yl)-4-fluoro-phenyl]-amide and compound 13: (S*)-5-methoxy-pyridine-2-carboxylic acid [3-(1-amino-3-difluoromethyl-3,4-dihydro-pyrrolo[1,2-a]pyrazin-3-yl)-4-fluoro-phenyl]-amide

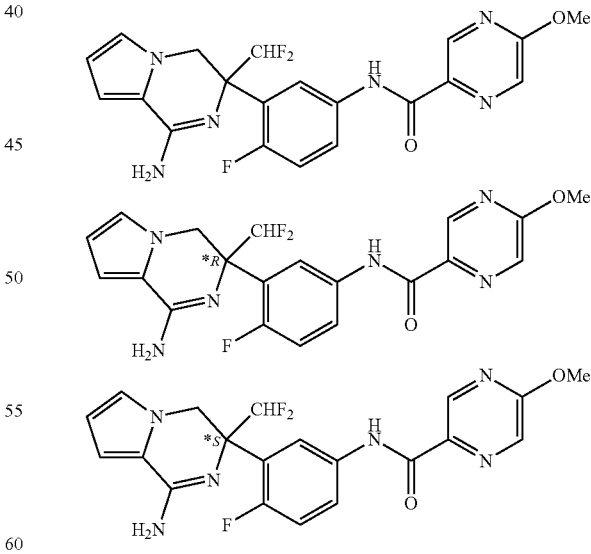

5-Methoxy-pyrazine-2-carboxylic acid (130 mg, 0.841 mmol) was added to a mixture of 4-(4,6-dimethoxy-1,3,5-triazin-2-yl)-4-methylmorpholinium chloride (233 mg, 0.841 mmol) in MeOH (4 mL). The mixture was stirred for 5 min at room temperature, then cooled to 0° C. and intermediate A53 (225 mg, 0.765 mmol) in MeOH (4 mL)

was added. The mixture was stirred at room temperature for 16 hours, then treated with sat. $Na_2CO_3$ and stirred for a few min. The solvent was concentrated, $H_2O$ was added and extracted with a mixture of DCM/MeOH (9:1). The organic layer was separated, dried ($MgSO_4$), filtered and concentrated in vacuo. The crude product was triturated with DCM and filtered to give a first batch of compound 11. The filtrates were evaporated and purified by flash column chromatography (silica gel; MeOH in DCM 0/100 to 7/93). The desired fractions were collected and the solvents evaporated in vacuo to yield a second batch of compound 11, that was combined with the previous one. The racemic compound was purified by chiral SFC on CHIRALCEL (OD-H 5 μm, 250×20 mm) Mobile phase (60% $CO_2$, 40% EtOH), yielding compound 12 (57 mg, 17% yield). $^1H$ NMR (500 MHz, DMSO-$d_6$) δ ppm 4.02 (s, 3H) 4.28 (br. d, J=13.0 Hz, 1H) 4.61 (br. d, J=13.0 Hz, 1H) 6.01 (dd, J=3.3, 2.7 Hz, 1H) 6.16 (t, J=55.5 Hz, 1H) 6.40 (br. s., 2H) 6.53 (d, J=2.6 Hz, 1H) 6.98 (br. s, 1H) 7.11-7.19 (m, 1H) 7.73-7.78 (m, 1H) 8.11 (dd, J=7.1, 2.7 Hz, 1H) 8.41 (d, J=1.2 Hz, 1H) 8.87 (d, J=1.2 Hz, 1H) 10.42 (br. s, 1H) and compound 13 (72 mg, 21% yield), for which the $^1H$ NMR spectrum was in agreement with the one of compound 12.

TABLE 1

| Co. No. | Method | $R^2$ | $R^4$ | $X^1$ | —L—Ar | $C_3$-stereochemistry/salt |
|---|---|---|---|---|---|---|
| 1 | B1 | H | $CH_3$ | CH | pyrimidin-5-yl | RS/$CF_3COOH$ |
| 2 | B2 | H | $CH_3$ | CH | 3,5-dichlorophenyl | RS |
| 3 | B3 | H | $CH_3$ | CH | -NH-C(O)-(5-chloropyridin-2-yl) | RS |
| 4 | B4 | H | $CH_3$ | CH | -NH-C(O)-(5-methoxypyrazin-2-yl) | RS |
| 5 | B5 | H | $CH_3$ | CF | -NH-C(O)-(5-chloropyridin-2-yl) | R |
| 6 | B6 | H | $CH_3$ | CF | -NH-C(O)-(5-cyanopyridin-2-yl) | R |

TABLE 1-continued
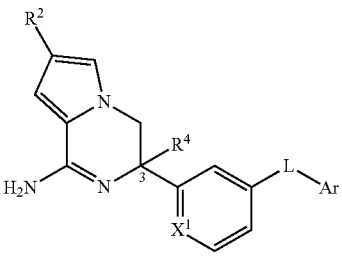
| Co. No. | Method | R² | R⁴ | X¹ | —L—Ar | C₃-stereochemistry/ salt |
|---|---|---|---|---|---|---|
| 7 | B7 | F | CH₃ | CF | 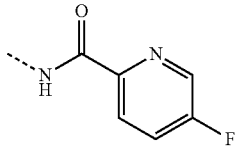 | R |
| 8 | B8 | F | CH₃ | CF | 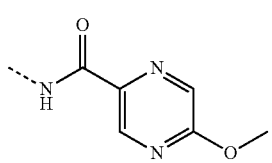 | R |
| 9 | B9 | CF₃ | CH₃ | CF | 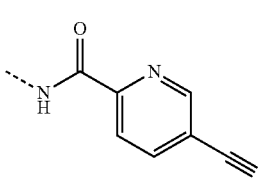 | R |
| 10 | B10 | CF₃ | CH₃ | CF | 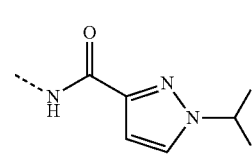 | R |
| 11 | B11 | CF₃ | CHF₂ | CF | 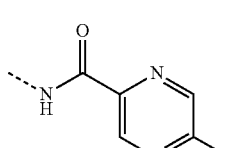 | RS |
| 12 | B11 | H | CHF₂ | CF | 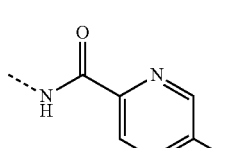 | *R |
| 13 | B11 | H | CHF₂ | CF | 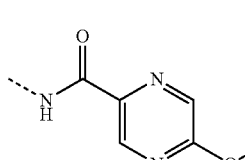 | *S |
| 14 | B9 | H | CHF₂ | CF | 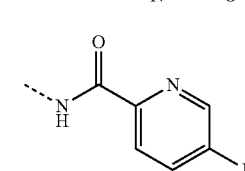 | RS |

TABLE 1-continued
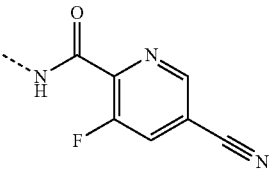
| Co. No. | Method | R² | R⁴ | X¹ | —L—Ar | C₃-stereochemistry/ salt |
|---|---|---|---|---|---|---|
| 15 | B9 | CF₃ | CH₃ | CF | 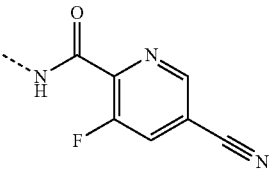 | R/CF₃COOH |
| 16 | B4 | F | CH₃ | CF | 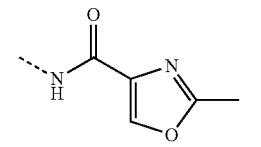 | R |
| 17 | B4 | F | CH₃ | CF | 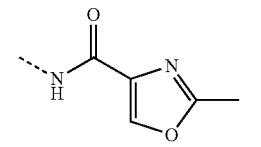 | R |
| 18 | B4 | F | CH₃ | CF | 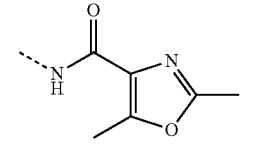 | R |
| 19 | B4 | CF₃ | CH₃ | CF | 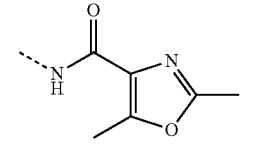 | R |
| 20 | B9 | CF₃ | CH₃ | CF |  | R/CF₃COOH |
| 21 | B9 | CF₃ | CH₃ | CF |  | R |
| 22 | B4 | CF₃ | CH₃ | CF | 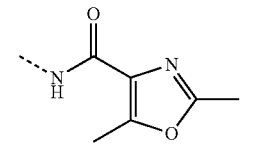 | R |

TABLE 1-continued
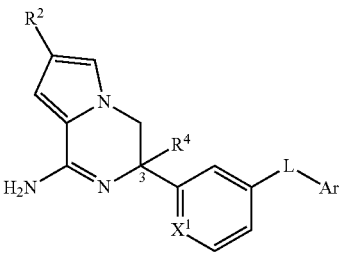
| Co. No. | Method | R² | R⁴ | X¹ | —L—Ar | C₃-stereochemistry/ salt |
|---|---|---|---|---|---|---|
| 23 | B9 | CF₃ | CH₃ | CF | 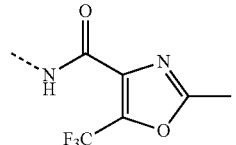 | R/CF₃COOH |
| 24 | B11 | CF₃ | CH₃OCH₂ | CF | 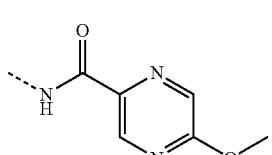 | RS |
| 25 | B11 | CF₃ | CH₃OCH₂ | CF | 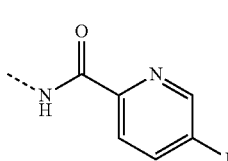 | RS |
| 26 | B11 | CF₃ | CH₃OCH₂ | CF | 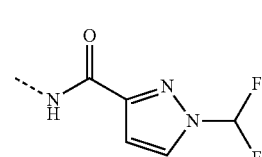 | RS |
| 27 | B11 | CF₃ | CH₃OCH₂ | CF | 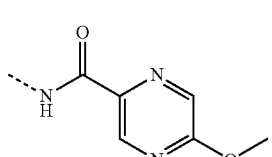 | *S |
| 28 | B11 | CF₃ | CH₃OCH₂ | CF | 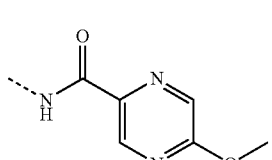 | *R |
| 29 | B11 | CF₃ | CH₃OCH₂ | CF | 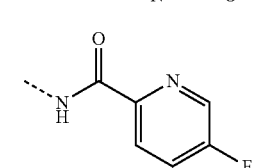 | *S |
| 30 | B11 | CF₃ | CH₃OCH₂ | CF | 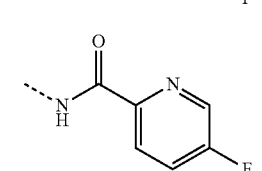 | *R |

TABLE 1-continued

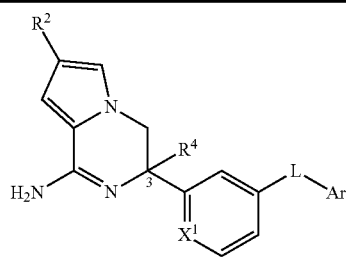

| Co. No. | Method | R² | R⁴ | X¹ | —L—Ar | C₃-stereochemistry/ salt |
|---|---|---|---|---|---|---|
| 31 | B11 | $CF_3$ | $CH_3OCH_2$ | CF | ![pyrazole carboxamide with N-CHF2] | *S |
| 32 | B11 | $CF_3$ | $CH_3OCH_2$ | CF | ![pyrazole carboxamide with N-CHF2] | *R |

Co. No. 1, 9, 15 and 20 were obtained as a trifluoroacetate salt (•CF₃COOH).

C. Analytical Part
LCMS

For (LC)MS-characterization of the compounds of the present invention, the following methods were used.

General Procedure A

The UPLC (Ultra Performance Liquid Chromatography) measurement was performed using an Acquity UPLC (Waters) system comprising a sampler organizer, a binary pump with degasser, a four column's oven, a diode-array detector (DAD) and a column as specified in the respective methods. The MS detector was configured with an electrospray ionization source. Mass spectra were acquired on a single quadrupole SQD detector (Waters) by scanning from 100 to 1000 in 0.1 second using an inter-channel delay of 0.08 seconds. The capillary needle voltage was 3.0 kV. The cone voltage was 25 V for positive ionization mode and 30 V for negative ionization mode. The source temperature was maintained at 140° C. Nitrogen was used as the nebulizer gas. Data acquisition was performed with MassLynx-Openlynx software.

Method 1:

In addition to the general procedure A: Reversed phase UPLC was carried out on a RRHD Eclipse Plus-C18 (1.8 µm, 2.1×50 mm) from Agilent, with a flow rate of 1.0 ml/min, at 50° C. without split to the MS detector. The gradient conditions used are: 95% A (6.5 mM NH₄AcO in H₂O/MeCN 95/5), 5% B (MeCN), to 40% A, 60% B in 3.8 min, to 5% A, 95% B in 4.6 min, kept till 5.0 min. Injection volume 2 µL.

General Procedure B

The HPLC measurement was performed using an HP 1100 (Agilent Technologies) system comprising a pump (quaternary or binary) with degasser, an autosampler, a column oven, a diode-array detector (DAD) and a column as specified in the respective methods. The MS detector (SQD, TOF) was configured with an electrospray ionization source. Nitrogen was used as the nebulizer gas. The source temperature was maintained at 140° C. Data acquisition was performed with MassLynx-Openlynx software.

B1: Mass spectra were acquired on a single quadrupole SQD detector by scanning from 100 to 1000 in 0.1 second using an inter-channel delay of 0.08 second. The capillary needle voltage was 3.0 kV. The cone voltage was 20 V for positive ionization mode and 30 V for negative ionization mode.

B2: Mass spectra were acquired on a Time of Flight (TOF) detector by scanning from 100 to 750 in 0.5 seconds using a dwell time of 0.3 seconds. The capillary needle voltage was 2.5 kV for positive ionization mode and 2.9 kV for negative ionization mode. The cone voltage was 20 V for both positive and negative ionization modes. Leucine-Enkephaline was the standard substance used for the lock mass calibration.

Method 2:

In addition to the general procedure B1: Reversed phase HPLC was carried out on an Eclipse Plus-C18 column (3.5 µm, 2.1×30 mm) from Agilent, with a flow rate of 1.0 mL/min, at 60° C. The gradient conditions used are: 95% A (6.5 mM NH₄AcO in H₂O/MeCN 95/5), 5% B (MeCN/MeOH 1/1), to 100% B in 5.0 min, kept to 5.15 min and equilibrated to initial conditions at 5.30 min until 7.0 min. Injection volume 2 µL.

Method 3:

In addition to the general procedure B2: Reversed phase HPLC was carried out on a Eclipse Plus-C18 column (3.5 µm, 2.1×30 mm) from Agilent, with a flow rate of 1.0 mL/min, at 60° C. The gradient conditions used are: 95% A (6.5 mM NH₄AcO in H₂O/MeCN 95/5), 5% B (MeCN/MeOH, 1/1) to 100% B in 5.0 min, kept till 5.15 min and equilibrated to initial conditions at 5.3 min until 7.0 min. Injection volume 2 µL.

Method 4:

In addition to the general procedure B2: Reversed phase HPLC was carried out on a Eclipse Plus-C18 column (3.5 µm, 2.1×30 mm) from Agilent, with a flow rate of 1.0 ml/min, at 60° C. The gradient conditions used are: 95% A (6.5 mM NH$_4$AcO in H$_2$O/MeCN 95/5), 5% B (MeCN), kept 0.2 min, to 100% B in 3.0 min, kept to 3.15 min and equilibrated to initial conditions at 3.3 min until 5.0 min. Injection volume 2 μL.

General Procedure C:

The LC measurement was performed using a UPLC (Ultra Performance Liquid Chromatography) Acquity (Waters) system comprising a binary pump with degasser, an autosampler, a diode-array detector (DAD) and a column as specified in the respective methods below, the column is hold at a temperature of 40° C. The MS detector was configured with an electrospray ionization source. Mass spectra were acquired on a triple quadrupole Quattro detector (Waters) by scanning from 100 to 1000 in 0.2 seconds using an inter-scan delay of 0.1 seconds. The capillary needle voltage was 3 kV and the source temperature was maintained at 130° C. Cone voltage was 20V for positive and negative ionization mode. Nitrogen was used as the nebulizer gas. Data acquisition was performed with MassLynx-Openlynx software (Waters).

Method 5:

In addition to the general procedureReversed phase UPLC was carried out on a Waters Acquity BEH (bridged ethylsiloxane/silica hybrid) Phenyl-Hexyl column (1.7 μm, 2.1× 100 mm) with a flow rate of 0.343 mL/min. Two mobile phases (mobile phase A: 95% 7 mM NH$_4$AcO/5% MeCN; mobile phase B: 100% MeCN) were employed to run a gradient condition from 84.2% A and 15.8% B (hold for 0.49 min) to 10.5% A and 89.5% B in 2.18 min, hold for 1.94 min and back to the initial conditions in 0.73 min, hold for 0.73 min. An injection volume of 2 ml was used.

Melting Points

Values are either peak values or melt ranges, and are obtained with experimental uncertainties that are commonly associated with this analytical method.

Mettler FP81HT/FP90 or FP62 Apparatus

For a number of compounds, melting points were determined in open capillary tubes either on a Mettler FP62 or a Mettler FP81HT/FP90 apparatus. Melting points were measured with a temperature gradient of 1, 3, 5 or 10° C./minute. Maximum temperature was 300° C. The melting point was read from a digital display.

For a number of compounds, melting points (m.p.) were determined with a WRS-2A melting point apparatus that was purchased from Shanghai Precision and Scientific Instrument Co. Ltd. Melting points were measured with a linear heating up rate of 0.2-5.0° C./minute. The reported values are melt ranges. The maximum temperature was 300° C.

TABLE 2

Analytical data - R$_t$ means retention time (in min), [M + H]$^+$ means the protonated mass of the compound, method refers to the method used for (LC)MS.

| Co. No. | R$_t$ | [M + H]$^+$ | Method | Melting Point |
|---|---|---|---|---|
| 1 | 0.83 | 304 | 1 | 87.2° C. (FP81HT/FP90) |
| 2 | 2.62 | 370 | 1 | 162.6° C. (FP81HT/FP90) |
| 3 | 1.83 | 380 | 1 | n.d. |
| 4 | 1.57 | 377 | 1 | 221° C. (FP81HT/FP90) |
| 5 | 2.81 | 398 | 3 | 197.3° C. (FP62) |
| 6 | 2.27 | 389 | 4 | 180° C. (FP81HT/FP90) |
| 7 | 1.68 | 400 | 1 | 197° C. (FP81HT/FP90) |
| 8 | 1.64 | 413 | 1 | 211° C. (FP81HT/FP90) |
| 9 | 2.09 | 457 | 1 | 150.2° C. (FP62) |
| 10 | 2.23 | 471 | 1 | 204.1° C. (FP62) |
| 11 | 2.51 | 431 | 5 | 252.7° C. (FP81HT/FP90) |

TABLE 2-continued

Analytical data - R$_t$ means retention time (in min), [M + H]$^+$ means the protonated mass of the compound, method refers to the method used for (LC)MS.

| Co. No. | R$_t$ | [M + H]$^+$ | Method | Melting Point |
|---|---|---|---|---|
| 12 | 2.50 | 431 | 5 | n.d. |
| 13 | 2.50 | 431 | 5 | n.d. |
| 14 | 1.97 | 418 | 1 | 224.9° C. (FP81HT/FP90) |
| 15 | 1.98 | 475 | 1 | 242.4° C. (FP62) |
| 16 | 1.38 | 386 | 1 | n.d. |
| 17 | 1.78 | 400 | 1 | 174° C. (FP81HT/FP90) |
| 18 | 2.08 | 454 | 1 | n.d. |
| 19 | 2.91 | 450 | 2 | >300° C. (FP62) |
| 20 | 1.84 | 436 | 1 | n.d. |
| 21 | 1.81 | 436 | 1 | n.d. |
| 22 | 2.15 | 438 | 1 | 160.6° C. (FP62) |
| 23 | 2.37 | 504 | 1 | 227° C. (FP62) |
| 24 | 2.26 | 493 | 1 | n.d. |
| 25 | 2.28 | 480 | 1 | n.d. |
| 26 | 2.09 | 501 | 1 | n.d. |
| 27 | 2.22 | 493 | 1 | 126.1° C. (FP81HT/FP90) |
| 28 | 2.21 | 493 | 1 | 121.8° C. (FP81HT/FP90) |
| 29 | 2.21 | 480 | 1 | 134.7° C. (FP81HT/FP90) |
| 30 | 2.22 | 480 | 1 | 137.6° C. (FP81HT/FP90) |
| 31 | 2.52 | 501 | 5 | 253.5° C. (FP81HT/FP90) |
| 32 | 2.54 | 501 | 5 | 250° C. (FP81HT/FP90) | n.d. means not determined

SFC-MS Methods:

General Procedure for SF-MS Methods:

The SFC measurement was performed using an Analytical SFC system from Berger instrument comprises a FCM-1200 dual pump fluid control module for delivering carbon dioxide (CO$_2$) and modifier, a CTC Analytics automatic liquid sampler, a TCM-20000 thermal control module for column heating from room temperature to 80° C. An Agilent 1100 UV photodiode array detector equipped with a high-pressure flow cell standing up to 400 bars was used. Flow from the column was split to a MS spectrometer. The MS detector was configured with an atmospheric pressure ionization source. The following ionization parameters for the Waters ZQ mass spectrophotometer are: corona: 9 μa, source temp: 140° C., cone: 30 V, probe temp 450° C., extractor 3 V, desolvatation gas 400 L/hr, cone gas 70 L/hr. Nitrogen was used as the nebulizer gas. Data acquisition was performed with a Waters-Micromass MassLynx-Openlynx data system.

Method 1:

In addition to the general procedure: The chiral separation in SFC was carried out on a CHIRALCEL OD-H DAICEL column (5 μm, 4.6×250 mm) at 35° C. with a flow rate of 3.0 mL/min. The mobile phase is CO$_2$, 40% EtOH (+0.3% iPrNH$_2$) hold 7 min in isocratic mode.

Method 2:

In addition to the general procedure: The chiral separation in SFC was carried out on a CHIRALPAK AD-H DAICEL column (10 μm, 4.6×250 mm) at 35° C. with a flow rate of 3.0 mL/min. The mobile phase is CO$_2$, 15% EtOH, 15% isopropanol (+0.3% iPrNH$_2$) hold 7 min in isocratic mode.

TABLE 3

Analytical SFC data - R$_t$ means retention time (in min), [M +H ]$^+$ means the protonated mass of the compound, method refers to the method used for SFC/MS analysis of enantiomerically pure compounds.

| Co. No. | R$_t$ | [M + H]$^+$ | UV Area % | Method | Isomer Elution Order* |
|---|---|---|---|---|---|
| 12 | 2.34 | 431 | 100 | 1 | A |
| 13 | 3.18 | 431 | 100 | 1 | B |

TABLE 3-continued

Analytical SFC data - $R_t$ means retention time (in min), [M +H ]+ means the protonated mass of the compound, method refers to the method used for SFC/MS analysis of enantiomerically pure compounds.

| Co. No. | $R_t$ | [M + H]+ | UV Area % | Method | Isomer Elution Order* |
|---|---|---|---|---|---|
| 31 | 1.80 | 501 | 100 | 2 | A |
| 32 | 2.64 | 501 | 100 | 2 | B |

*A means the first isomer that elutes. B means the second isomer that elutes.

Optical Rotations:

Optical rotations were measured on a Perkin-Elmer 341 polarimeter with a sodium lamp and reported as follows: $[\alpha]_\lambda^{t° C.}$ (c g/100 mL, solvent).

TABLE 4

Analytical data - Optical rotation values for enantiomerically pure compounds.

| Co. No. | $\alpha_D$ (°) | Wavelength (nm) | Concentration w/v % | Solvent | Temp. (° C.) |
|---|---|---|---|---|---|
| 5 | 103.6 | 589 | 0.45 | DMF | 20 |
| 6 | 91.4 | 589 | 0.47 | DMF | 20 |
| 7 | 84.7 | 589 | 0.63 | DMF | 20 |
| 8 | 104.0 | 589 | 0.53 | DMF | 20 |
| 9 | 111.7 | 589 | 0.53 | DMF | 20 |
| 12 | 198.0 | 589 | 0.26 | DMF | 20 |
| 13 | −207.5 | 589 | 0.86 | DMF | 20 |
| 15 | 108.7 | 589 | 0.55 | DMF | 20 |
| 16 | −24.4 | 589 | 0.54 | DMF | 20 |
| 17 | −28.3 | 589 | 0.53 | DMF | 20 |
| 18 | −45.4 | 589 | 0.56 | DMF | 20 |
| 27 | −142 | 589 | 0.5 | DMF | 20 |
| 28 | 134.2 | 589 | 0.48 | DMF | 20 |
| 29 | 130.1 | 589 | 0.49 | DMF | 20 |
| 30 | −110.7 | 589 | 0.5 | EtOH | 20 |
| 31 | −109.8 | 589 | 0.48 | DMF | 20 |
| 32 | 107.9 | 589 | 0.47 | DMF | 20 |

Pharmacological Examples

The compounds provided in the present invention are inhibitors of the β-site APP-cleaving enzyme 1 (BACE1). Inhibition of BACE1, an aspartic protease, is believed to be relevant for treatment of Alzheimer's Disease (AD). The production and accumulation of β-amyloid peptides (Aβ) from the β-amyloid precursor protein (APP) is believed to play a key role in the onset and progression of AD. Aβ is produced from the amyloid precursor protein (APP) by sequential cleavage at the N- and C-termini of the Aβ domain by β-secretase and γ-secretase, respectively.

Compounds of Formula (I) are expected to have their effect substantially at BACE1 by virtue of their ability to inhibit the enzymatic activity. The behaviour of such inhibitors tested using a biochemical Fluorescence Resonance Energy Transfer (FRET) based assay and a cellular αlisa assay in SKNBE2 cells described below and which are suitable for the identification of such compounds, and more particularly the compounds according to Formula (I), are shown in Table 1.

Biochemical FRET Based Assay

This assay is a Fluorescence Resonance Energy Transfer Assay (FRET) based assay. The substrate for this assay is an APP derived 13 amino acids peptide that contains the 'Swedish' Lys-Met/Asn-Leu mutation of the amyloid precursor protein (APP) β-secretase cleavage site. This substrate also contains two fluorophores: (7-methoxy-coumarin-4-yl) acetic acid (Mca) is a fluorescent donor with excitation wavelength at 320 nm and emission at 405 nm and 2,4-Dinitrophenyl (Dnp) is a proprietary quencher acceptor. The distance between those two groups has been selected so that upon light excitation, the donor fluorescence energy is significantly quenched by the acceptor, through resonance energy transfer. Upon cleavage by BACE1, the fluorophore Mca is separated from the quenching group Dnp, restoring the full fluorescence yield of the donor. The increase in fluorescence is linearly related to the rate of proteolysis (Koike H et al. J. Biochem. 1999, 126, 235-242).

Briefly in a 384-well format recombinant BACE1 protein in a final concentration of 1 µg/ml is incubated for 120 min at room temperature with 10 µm substrate in incubation buffer (40 mM Citrate buffer pH 5.0, 0.04% PEG, 4% DMSO) in the absence or presence of compound. Next the amount of proteolysis is directly measured by fluorescence measurement at T=0 and T=120 (excitation at 320 nm and emission at 405 nm). Results are expressed in RFU, as difference between T120 and T0

A best-fit curve is fitted by a minimum sum of squares method to the plot of % Controlmin versus compound concentration. From this an IC50 value (inhibitory concentration causing 50% inhibition of activity) can be obtained.

LC = Median of the low control values

= Low control: Reaction without enzyme

HC = Median of the High control values

= High control: Reaction with enzyme

% Effect = 100 − [(sample − LC)/(HC − LC) * 100]

% Control = (sample/HC) * 100

% Controlmin = (sample − LC)/(HC − LC) * 100

The following exemplified compounds were tested essentially as described above and exhibited the following the activity:

TABLE 5

| Co. No. | Biochemical FRET based assay pIC$_{50}$ |
|---|---|
| 1 | 4.92 |
| 2 | 5.43 |
| 3 | 6.87 |
| 4 | 6.63 |
| 5 | 7.43 |
| 6 | 7.71 |
| 7 | 7.38 |
| 8 | 7.48 |
| 9 | 7.47 |
| 10 | 7.32 |
| 11 | 6.97 |
| 12 | 7.43 |
| 13 | 4.74 |
| 14 | 6.76 |
| 15 | 7.44 |
| 16 | 7.31 |
| 17 | 7.17 |
| 18 | 7.08 |
| 19 | 6.75 |
| 20 | 6.99 |
| 21 | 7.02 |
| 22 | 6.65 |
| 23 | 6.74 |
| 24 | 5.50 |

TABLE 5-continued

| Co. No. | Biochemical FRET based assay pIC$_{50}$ |
|---|---|
| 25 | 5.30 |
| 26 | 5.54 |
| 27 | <4.3 |
| 28 | 5.72 |
| 29 | 5.69 |
| 30 | 4.46 |
| 31 | <4.3 |
| 32 | 5.76 |

Cellular αlisa Assay in SKNBE2 Cells

In two αlisa assays the levels of Aβtotal and Aβ42 produced and secreted into the medium of human neuroblastoma SKNBE2 cells are quantified. The assay is based on the human neuroblastoma SKNBE2 expressing the wild type Amyloid Precursor Protein (hAPP695). The compounds are diluted and added to these cells, incubated for 18 hours and then measurements of Aβ42 and Aβtotal are taken. Aβtotal and Aβ42 are measured by sandwich αlisa. αlisa is a sandwich assay using biotinylated antibody AbN/25 attached to streptavidin coated beads and antibody Ab4G8 or cAb42/26 conjugated acceptor beads for the detection of Aβtotal and Aβ42 respectively. In the presence of Aβtotal or Aβ42, the beads come into close proximity. The excitation of the Donor beads provokes the release of singlet oxygen molecules that triggers a cascade of energy transfer in the Acceptor beads, resulting in light emission. Light emission is measured after 1 hour incubation (excitation at 650 nm and emission at 615 nm).

A best-fit curve is fitted by a minimum sum of squares method to the plot of % Controlmin versus compound concentration. From this an 1050 value (inhibitory concentration causing 50% inhibition of activity) can be obtained.

$LC$ = Median of the low control values
  = Low control: cells preincubated without compound, without biotinylated Ab in the αlisa $HC$ = Median of the High control values
  = High Control: cells preincubated without compound % Effect = $100 - [(sample - LC)/(HC - LC) * 100]$ % Control = $(sample/HC) * 100$ % Controlmin = $(sample - LC)/(HC - LC) * 100$ The following exemplified compounds were tested essentially as described above and exhibited the following the activity:

TABLE 6

| Co. No. | Cellular αlisa assay in SKNBE2 cells Aβ42 pIC$_{50}$ | Cellular αlisa assay in SKNBE2 cells Aβtotal pIC$_{50}$ |
|---|---|---|
| 1 | 5.4 | 5.41 |
| 2 | 5.35 | 5.37 |
| 3 | 7 | 7.02 |
| 4 | 6.96 | 7.03 |
| 5 | 8.53 | 8.55 |
| 6 | 8.8 | 8.85 |
| 7 | 8.18 | 8.25 |
| 8 | 8.66 | 8.69 |
| 9 | 7.92 | 7.97 |
| 10 | 7.87 | 7.9 |
| 11 | 7.96 | 8.02 |
| 12 | 7.85 | 7.9 |
| 13 | 5.63 | 5.62 |
| 14 | 7.43 | 7.45 |
| 15 | 8.03 | 8.05 |
| 16 | 7.69 | 7.71 |
| 17 | 7.49 | 7.47 |
| 18 | 7.50 | 7.51 |
| 19 | 7.18 | 7.20 |
| 20 | 7.62 | 7.63 |
| 21 | 7.83 | 7.79 |
| 22 | 7.31 | 7.32 |
| 23 | 7.12 | 7.11 |
| 24 | 6.30 | 6.35 |
| 25 | 6.04 | 6.07 |
| 26 | 6.30 | 6.27 |
| 27 | <5 | <5 |
| 28 | 6.53 | 6.52 |
| 29 | 6.32 | 6.33 |
| 30 | <5 | <5 |
| 31 | <5 | <5 |
| 32 | 6.54 | 6.53 |

Demonstration of In Vivo Efficacy

Aβ peptide lowering agents of the invention can be used to treat AD in mammals such as humans or alternatively demonstrating efficacy in animal models such as, but not limited to, the mouse, rat, or guinea pig. The mammal may not be diagnosed with AD, or may not have a genetic predisposition for AD, but may be transgenic such that it overproduces and eventually deposits Aβ in a manner similar to that seen in humans afflicted with AD.

Aβ peptide lowering agents can be administered in any standard form using any standard method. For example, but not limited to, Aβ peptide lowering agents can be in the form of liquid, tablets or capsules that are taken orally or by injection. Aβ peptide lowering agents can be administered at any dose that is sufficient to significantly reduce levels of Aβ peptides in the blood, blood plasma, serum, cerebrospinal fluid (CSF), or brain.

To determine whether acute administration of an Aβ42 peptide lowering agent would reduce Aβ peptide levels in vivo, non-transgenic rodents, e.g. mice or rats were used. Animals treated with the Aβ peptide lowering agent were examined and compared to those untreated or treated with vehicle and brain levels of soluble Aβ42 and total Aβ were quantitated by standard techniques, for example, using ELISA. Treatment periods varied from hours (h) to days and were adjusted based on the results of the Aβ42 lowering once a time course of onset of effect could be established.

A typical protocol for measuring Aβ42 lowering in vivo is shown but it is only one of many variations that could be used to optimize the levels of detectable Aβ. For example, Aβ peptide lowering compounds were formulated in 20% hydroxypropyl β cyclodextrin. The Aβ peptide lowering agents were administered as a single oral dose (p.o.) or a single subcutaneous dose (s.c.) to overnight fasted animals. After a certain time, usually 2 or 4 h (as indicated in Table 7), the animals were sacrificed and Aβ42 levels were analysed.

Blood was collected by decapitation and exsanguinations in EDTA-treated collection tubes. Blood was centrifuged at 1900 g for 10 min (min) at 4° C. and the plasma recovered and flash frozen for later analysis. The brain was removed from the cranium and hindbrain. The cerebellum was removed and the left and right hemisphere were separated. The left hemisphere was stored at −18° C. for quantitative analysis of test compound levels. The right hemisphere was rinsed with phosphate-buffered saline (PBS) buffer and immediately frozen on dry ice and stored at −80° C. until homogenization for biochemical assays.

Mouse brains from non-transgenic animals were resuspended in 8 volumes of 0.4% DEA (diethylamine)/50 mM NaCl containing protease inhibitors (Roche-11873580001 or 04693159001) per gram of tissue, e.g. for 0.158 g brain, add 1.264 ml of 0.4% DEA. All samples were homogenized in the FastPrep-24 system (MP Biomedicals) using lysing matrix D (MPBio #6913-100) at 6 m/s for 20 seconds. Homogenates were centrifuged at 221.300×g for 50 min. The resulting high speed supernatants were then transferred to fresh eppendorf tubes. Nine parts of supernatant were neutralized with 1 part 0.5 M Tris-HCl pH 6.8 and used to quantify Aβtotal and Aβ42.

To quantify the amount of Aβtotal and Aβ42 in the soluble fraction of the brain homogenates, Enzyme-Linked-Immunosorbent-Assays were used. Briefly, the standards (a dilution of synthetic Aβ1-40 and Aβ1-42, Bachem) were prepared in 1.5 ml Eppendorf tube in Ultraculture, with final concentrations ranging from 10000 to 0.3 pg/ml. The samples and standards were co-incubated with HRPO-labelled N-terminal antibody for Aβ42 detection and with the biotinylated mid-domain antibody 4G8 for Aβtotal detection. 50 µl of conjugate/sample or conjugate/standards mixtures were then added to the antibody-coated plate (the capture antibodies selectively recognize the C-terminal end of Aβ42, antibody JRF/cAβ42/26, for Aβ42 detection and the N-terminus of Aβ, antibody JRF/rAβ/2, for Aβtotal detection). The plate was allowed to incubate overnight at 4° C. in order to allow formation of the antibody-amyloid complex. Following this incubation and subsequent wash steps the ELISA for Aβ42 quantification was finished by addition of Quanta Blu fluorogenic peroxidase substrate according to the manufacturer's instructions (Pierce Corp., Rockford, Ill.). A reading was performed after 10 to 15 min (excitation 320 nm/emission 420 nm).

For Aβtotal detection, a Streptavidine-Peroxidase-Conjugate was added, followed 60 min later by an additional wash step and addition of Quanta Blu fluorogenic peroxidase substrate according to the manufacturer's instructions (Pierce Corp., Rockford, Ill.). A reading was performed after 10 to 15 min (excitation 320 nm/emission 420 nm).

In this model at least 20% Aβ42 lowering compared to untreated animals would be advantageous.

The following exemplified compounds were tested essentially as described above and exhibited the following activity:

We claim:
1. A compound of Formula (I)

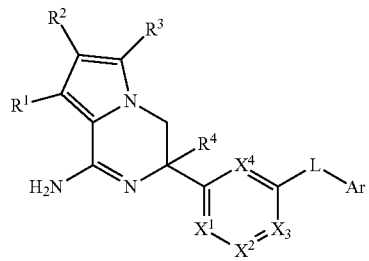

or a tautomer or a stereoisomeric form thereof, wherein
$R^1$, $R^2$, and $R^3$ are independently selected from the group consisting of hydrogen, halo, cyano, $C_{1-3}$alkyl, monohalo-$C_{1-3}$alkyl, polyhalo-$C_{1-3}$alkyl, and $C_{3-6}$cycloalkyl;
$R^4$ is selected from the group consisting of hydrogen, $C_{1-3}$alkyl, methoxymethyl, $C_{3-6}$ cycloalkyl, monohalo-$C_{1-3}$alkyl, polyhalo-$C_{1-3}$alkyl, homoaryl, and heteroaryl;
$X^1$, $X^2$, $X^3$, and $X^4$ are independently $C(R^5)$ or N, provided that no more than two thereof represent N;
$R^5$ is selected from the group consisting of hydrogen, halo, cyano, $C_{1-3}$alkyl, monohalo-$C_{1-3}$alkyl, polyhalo-$C_{1-3}$alkyl, and $C_{3-6}$cycloalkyl;
L is a bond or —NHCO—;
Ar is homoaryl or heteroaryl;
wherein homoaryl is phenyl or phenyl substituted with one, two or three substituents selected from the group consisting of halo, cyano, $C_{1-3}$alkyl, $C_{1-3}$alkyloxy, monohalo-$C_{1-3}$alkyl, polyhalo-$C_{1-3}$ alkyl, monohalo-$C_{1-3}$alkyloxy, and polyhalo-$C_{1-3}$alkyloxy;
heteroaryl is selected from the group consisting of pyridyl, pyrimidyl, pyrazinyl, pyridazyl, furanyl, thienyl, pyrrolyl, pyrazolyl, imidazolyl, triazolyl, thiazolyl, thiadiazolyl, oxazolyl, and oxadiazolyl, each optionally substituted with one, two or three substituents selected from the group consisting of halo, cyano, $C_{1-3}$alkyl, $C_{1-3}$alkyloxy, monohalo-$C_{1-3}$alkyl, polyhalo-$C_{1-3}$alkyl, monohalo-$C_{1-3}$alkyloxy, and polyhalo-$C_{1-3}$alkyloxy; or a pharmaceutically acceptable salt thereof.

2. The compound of claim 1 wherein,
$R^1$, $R^2$ and $R^3$ are independently selected from hydrogen and $C_{1-3}$alkyl;
$X^1$, $X^2$, $X^3$, and $X^4$ are independently $C(R^5)$ wherein each $R^5$ is selected from hydrogen and halo;
L is a bond or —NHCO—;
Ar is homoaryl or heteroaryl;
wherein homoaryl is phenyl or phenyl substituted with one or two substituents selected from the group consisting of halo, cyano, $C_{1-3}$alkyl, $C_{1-3}$alkyloxy, and polyhalo-$C_{1-3}$alkyloxy;

TABLE 7

| Co. No. | Aβ42 (%Ctrl)_Mean | Aβtotal (%Ctrl)_Mean | Dose | Route of administration | Time after administration |
|---|---|---|---|---|---|
| 7 | 73 | 99 | 30 mg/kg | p.o. | 4 h. | p.o. means oral heteroaryl is selected from the group consisting of pyridyl, pyrimidyl, and pyrazinyl, each optionally substituted with one or two substituents selected from the group consisting of halo, cyano, $C_{1-3}$alkyl, $C_{1-3}$alkyloxy, and polyhalo-$C_{1-3}$alkyloxy; or a pharmaceutically acceptable salt thereof.

3. The compound of claim 1 wherein, $R^1$, $R^2$ and $R^3$ are hydrogen;

$X^1$ is CF;

$X^2$, $X^3$, and $X^4$ are CH;

L is a bond or —NHCO—;

Ar is homoaryl or heteroaryl;

wherein homoaryl is phenyl substituted with chloro;

heteroaryl is selected from the group consisting of pyridyl and pyrimidyl, each optionally substituted with one or two substituents selected from the group consisting of chloro, fluoro, cyano, methyl, and methoxy; or a pharmaceutically acceptable salt thereof.

4. The compound of claim 1 wherein the carbon atom substituted with $R^4$ has the R-configuration.

5. The compound of claim 1 wherein $R^1$ and $R^3$ are hydrogen, $R^2$ is hydrogen, fluoro, or trifluoromethyl;

$R^4$ is methyl or difluoromethyl;

$X^1$ is CH or CF;

$X^2$, $X^3$, and $X^4$ are CH;

L is —NHCO—;

Ar is 5-chloropyrid-2-yl, 5-cyanopyrid-2-yl, 5-fluoropyrid-2-yl, 5-cyano-3-fluorooropyrid-2-yl, 5-methoxypyrazin-2-yl or 1-difluoromethylpyrazol-3-yl; or a pharmaceutically acceptable salt thereof.

6. A pharmaceutical composition comprising a therapeutically effective amount of a compound of claim 1 and a pharmaceutically acceptable carrier.

7. A process for preparing the pharmaceutical composition of claim 6, comprising admixing a therapeutically effective amount of a compound of claim 1 with a pharmaceutically acceptable carrier.

8. A method of inhibiting beta-secretase in a subject comprising administering to a subject in need thereof, a therapeutically effective amount of a compound of claim 1.

* * * * *